(12) United States Patent
Bogevig et al.

(10) Patent No.: US 7,829,707 B2
(45) Date of Patent: Nov. 9, 2010

(54) PYRROLO [3,2-D]PYRIMIDIN-4-ONE DERIVATIVES AND THEIR USE IN THERAPY

(75) Inventors: Anders Bogevig, Sodertalje (SE); Yvonne Lo-Alfredsson, Sodertalje (SE); Donald Pivonka, Wilmington, DE (US); Anna-Karin Tiden, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 565 days.

(21) Appl. No.: 11/720,913

(22) PCT Filed: Dec. 5, 2005

(86) PCT No.: PCT/SE2005/001835

§ 371 (c)(1), (2), (4) Date: Jun. 5, 2007

(87) PCT Pub. No.: WO2006/062465

PCT Pub. Date: Jun. 15, 2006

(65) Prior Publication Data

US 2008/0221136 A1   Sep. 11, 2008

(30) Foreign Application Priority Data

Dec. 6, 2004  (SE) ..................... 0402972
May 13, 2005 (SE) ..................... 0501093

(51) Int. Cl.
- C07D 487/04 (2006.01)
- A61K 31/519 (2006.01)
- A61P 9/10 (2006.01)
- A61P 29/00 (2006.01)

(52) U.S. Cl. .................... 544/280; 514/265.1

(58) Field of Classification Search ................ 544/280; 514/265.1
See application file for complete search history.

(56) References Cited

U.S. PATENT DOCUMENTS

| | | | |
|---|---|---|---|
| 3,135,753 | A | 6/1964 | Hitchings et al. |
| 4,820,709 | A | 4/1989 | Hofer |
| 5,173,491 | A | 12/1992 | Kamoun et al. |
| 5,489,598 | A | 2/1996 | Connor et al. |
| 5,716,967 | A | 2/1998 | Kleinman |
| 5,756,511 | A | 5/1998 | West et al. |
| 5,976,823 | A | 11/1999 | Wu |
| 6,025,361 | A | 2/2000 | Cavalla et al. |
| 6,046,019 | A | 4/2000 | Goumeniouk et al. |
| 6,066,641 | A | 5/2000 | Cavalla et al. |
| 6,294,541 | B1 | 9/2001 | Cavalla et al. |
| 6,319,928 | B1 | 11/2001 | Chasin et al. |
| 7,108,997 | B2 | 9/2006 | Kettle |
| 2004/0022871 | A1 | 2/2004 | Mainnemare |
| 2004/0029871 | A1 | 2/2004 | Thong et al. |
| 2005/0070558 | A1 | 3/2005 | Vidal Juan et al. |
| 2005/0234036 | A1 | 10/2005 | Hanson et al. |
| 2007/0032468 | A1 | 2/2007 | Kettle et al. |
| 2007/0093483 | A1 | 4/2007 | Svensson et al. |

FOREIGN PATENT DOCUMENTS

| | | |
|---|---|---|
| CN | 1013676 | 8/1991 |
| EP | 0010531 | 6/1982 |
| EP | 0359505 | 3/1990 |
| EP | 0430300 | 6/1991 |
| EP | 0452926 | 3/1996 |
| EP | 01016407 | 5/2006 |
| JP | 02160235 | 6/1990 |
| WO | 8906125 | 7/1989 |
| WO | 9500516 | 1/1995 |
| WO | 9618400 | 6/1996 |
| WO | 9914204 | 3/1999 |
| WO | 9917773 | 4/1999 |
| WO | 9936073 | 7/1999 |
| WO | 9940091 | 8/1999 |
| WO | 0051598 | 9/2000 |
| WO | 0059449 | 10/2000 |
| WO | 0185146 | 11/2001 |
| WO | 0206272 | 1/2002 |
| WO | 0208237 | 1/2002 |
| WO | 02066447 | 8/2002 |
| WO | 02090575 | 11/2002 |
| WO | 03000694 | 1/2003 |
| WO | 03082873 | 10/2003 |
| WO | 03089430 | 10/2003 |
| WO | 2004096781 | 11/2004 |
| WO | 2005037835 | 4/2005 |

(Continued)

OTHER PUBLICATIONS

Lim et. al. (Journal of Organic Chemistry, 1979, 44(22) pp. 3826-3829).*

(Continued)

*Primary Examiner*—James O Wilson
*Assistant Examiner*—Susanna Moore

(57) ABSTRACT

There are disclosed novel compounds of formula (I) wherein $R^1$, $R^{12}$, L, X and Y are as defined in the specification, and pharmaceutically acceptable salts thereof; together with processes for their preparation, compositions containing them and their use in therapy. The compounds are inhibitors of the enzyme MPO and are thereby particularly useful in the treatment or prophylaxis of neuroinflammatory disorders, cardiovascular disorders and respiratory disorders.

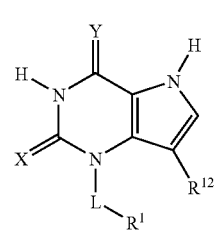

1 Claim, No Drawings

FOREIGN PATENT DOCUMENTS

| WO | 2005042534 | 5/2005 |
|---|---|---|
| WO | 2005077950 | 8/2005 |
| WO | 2006045564 | 5/2006 |
| WO | 2006046910 | 5/2006 |
| WO | 2007142576 | 12/2007 |

OTHER PUBLICATIONS

Grehn (Chemica Scripta, 1980, 16(3) pp. 77-84).*
Parry et al., "Myeloperoxidase Deficiency, Prevalence and Clinical Signficance," Ann Int Med., 1981, vol. 95, pp. 293-301.
Pesci et al., "Inflammatory Cells and Mediators in Bronchial Lavage of Patients with Chronic Obstructive Pulmonary Disease," European Respiratory Journal, 1998, vol. 12, pp. 380-386.
Peskin et al., "Kinetics of the Reactions of Hypochlorous Acid and Amino Acid Chloramines with Thiols, Methionine, and Ascorbate," Free Radical Biology and Medicine, 2001, vol. 30(5), pp. 572-579.
Peskin et al., "Chlorine Transfer Between Glycine, Taurine, and Histamine: Reaction Rates and Impact of Cellular Reactivity," Free Radical Biology and Medicine, 2004, vol. 37(10), pp. 1622-1630.
Rao et al., "Synthesis of 5,7-Disubstituted-4-Beta-D-ribofuranosylpyrazolo[4,3-d]-pyrimidines and 2,4-Disubstituted-1-Beta-D-ribofuranosylpyrrolo[3,2-d]-pyrimidines as Congeners of Uridine and Cytidine," J. Heterocyclic Chemistry, 1992, vol. 29, pp. 343-354.
Rosen et al., "Oxidation of *Escherichia coli* Iron Centers by the Myeloperoxidase-mediated Microbicidal System," Journal of Biological Chemistry, 1982, vol. 257(22), pp. 13731-13735.
Shao et al., "Tyrosine 192 in Apolipoprotein A-I is the Major Site of Nitration and Chlorination by Myeloperoxidase, but only Chlorination Markedly Impairs ABCA1-Dependent Cholesterol Transport," Journal of Biological Chemistry, 2005, vol. 280(7), pp. 5983-5993.
Sugiyama, S. et al., "Macrophage Myeloperoxidase Regulation by Granulocyte Macrophage Colony-Stimulating Factor in Human Atherosclerosis and Implications in Acute Coronary Syndromes," Am J Pathol, 2001, pp. 879-891, vol. 158, No. 3.
Suzuki et al., "Assay method for myeloperoxidase in human polymorphonuclear leukocytes," Analytical Biochemistry, 1983, vol. 132, pp. 345-352.
Suzuki et al., "Synthesis and Cyclic AMP Phosphodiesterase 4 Isoenzyme Inhibitory Activity of Heterocycle Condensed Purines," Chem. Pharm. Bull., 2002, vol. 50(9), pp. 1163-1168.
Van Galen et al., "A Binding Site Model and Structure-Activity Relationships for the Rat A3 Adenosine Receptor," Molecular Pharmacology, 1994, vol. 45, pp. 1101-1111.
Van Zyl et al., "Interaction of methylxanthines with myeloperoxidase. An anti-inflammatory mechanism," Intnl J. of Biochem, 1992, vol. 24(6), pp. 929-935.
Wacker et al., "CCR3 Antagonists: A Potential New Therapy for the Treatment of Asthma. Discovery and Structure—Activity Relationships," Bioorganic & Medicinal Chemistry Letters, 2002, vol. 12, pp. 1785-1789.
Wolfe et al., "Scope and Limitations of the Pd/BINAP-Catalyzed Amination or Aryl Bromides," Journal of Organic Chemistry, 2000, vol. 65, pp. 1144-1157.
Woo et al., "Inhibitors of Human Purine Nucleoside Phosphorylase. Synthesis and Biological Activities of 8-Amino-3-benzylhypoxanthine and Related Analogues," J. Med. Chem., 1992; vol. 35, pp. 1451-1457.
Wooldridge et al., "The Synthesis of Some 6-Thioxanthines," J. Chem. Soc., 1962, pp. 1863-1868.
Yang et al., "Granulocyte Function Disorders: Aspects of Development, Genetics and Management," Pediatric Infectious Disease Journal, 2001, vol. 20, pp. 889-900.
Yong et al., "Metalloproteinases in Biology and Pathology of the Nervous System," Nature Reviews Neuroscience, 2001, vol. 2(7), pp. 502-511.
Zhang, R. et al.,"Association Between Myeloperoxidase Levels and Risk of Coronary Artery Disease," Jama, 2001, pp. 2136-2142, vol. 286, No. 17.
Zheng et al., "Localization of Nitration and Chlorination Sites on Apolipoprotein A-I Catalyzed by Myeloperoxidase in Human Atheroma and Associated Oxidative Impairment in ABCA1-Dependent Cholesterol Efflux from Macrophages," Journal of Biological Chemistry, 2005, vol. 280(1), pp. 38-47.
Zheng et al., "Apolipoprotein A-I is a Selective Target for Myeloperoxidase-Catalyzed Oxidation and Functional Impairment in Subjects with Cardiovascular Disease," Journal of Clinical Investigation, 2004, vol. 114(4), pp. 529-541.
STN Intnl, CAPLUS Accession No. 1968:434597, Doc No. 69:34597, Dietz et al., "The hypnotic properties of 8-ethylthio-6-thiotheophylline sodium" & Toxicology and Applied Pharm., 1968, vol. 12, pp. 202-206.
STN Intnl, CAPLUS Accession No. 1966:420839, Doc No. 65:20839, Dietz et al., "The synthesis and pharmacologic evaluation of a series of 8-alkylthio-thiated theophyylines" & J. of Med Chem., 1966, vol. 9(4), pp. 500-506.
STN Intnl, CAPLUS Accession No. 1966:35888, Doc No. 64:35888, Dietz et al., "Synthesis of some 8-alkylthio-2-thiotheophyllines and 8-alkylthio-6-thiotheophyllines" & J. of Med Chem., 1966, vol. 9(1), p. 160.
STN Intnl CAPLUS Accession No. 1974:82889, No. 80:82889, Reichman, Uri et al., "Tautomerism, ionization and methylation of 2(methylthio)- and 2,8-bis(methyl-thio)hypoxanthines" & J. of the Chem. Soc., Perkin Transactions 1:Organic & BioOrganic Chem, 1972-1999, (22), 2647-55, 1973.
STN Intnl, File CAPLUS Accession No. 1984:630460, Doc No. 101:230460, Talukdar, P.B. et al., "Studies on ring-fused mesoionic thiazolo(3,2-a) imidazolo(4,5-d)pyrimidine derivatives," & Indian J. of Chem, Section B: Organic Chem. Including Medicinal Chem, 23B(4), pp. 316-320, 1984.
STN Intnl, file Registry, 2H-Purin-2-one, 1,3,6,7-tetrahydro-8-(methylthio)-6-thioxo-(9CI) Reg No. 500336-85-6, 2004.
STN Intnl, file Registry, "2-H-Purin-2-one, 1,3,6,7-tetrahydro-8-(propylthio)-6-thioxo-, sodium salt (9CI)" Reg No. 5784-48-5, 2004.
STN Intnl, file Registry, "1H-Purine-2,6-dithione, 3,7-dihydro-1,3-dimethyl-8-(methylthio)-, sodium salt (9CI)" Reg No. 5779-07-7, 2004.
STN Intnl, file Registry, "2h-Purin-2-one, 8-[(1-ethylbutyl)thio]-1,3,6,7-tetrahydro-1,3-dimethyl-6-thioxo-, sodium salt (9CI)", Reg. No. 5779-06-6, 2004.
STN printout for Registry No. 582-33-2: 3-Aminobenzoic acid ethyl ester, 2007.
STN Intnl, Registry No. 2487-40-3, 2007.
International Search Report issued for PCT/SE2005/001835 on Feb. 21, 2006.
English abstract for JP 02160235.
English abstract for WO 2002006272.
Non-final OA issued for U.S. Appl. No. 10/511,537 on Apr. 27, 2007, AstraZeneca Ref. 100647.
OA issued for U.S. Appl. No. 10/511,537 on Aug. 27, 2007, AstraZeneca Ref. 100647.
Advisory Action issued for U.S. Appl. No. 10/275,824 on May 22, 2007, AstraZeneca Ref. 100046.
Final OA issued for U.S. Appl. No. 10/275,824 on Feb. 8, 2007, AstraZeneca Ref. 100046.
Non-final OA issued for 10/275,824 on Jun. 19, 2006, AstraZeneca Ref. 100046.
Advisory Action issued for U.S. Appl. No. 10/275,824 on Mar. 15, 2006, AstraZeneca Ref. 100046.
Final OA issued for U.S. Appl. No. 10/275,824 on Nov. 30, 2005, AstraZeneca Ref. 100046.
Non-final OA issued for U.S. Appl. No. 10/275,824 on Jun. 17, 2005, AstraZeneca Ref. 100046.
U.S. Appl. No. 11/577,833, filed Apr. 24, 2007.
U.S. Appl. No. 11/756,967, filed Jun. 1, 2007.
Aaron, S D et al., "Granulocyte Inflammatory Markers and Airway Infection during Acute Exacerbation of Chronic Obstructive Pulmonary Disease," Am J Respir Crit Care Med., 2001, pp. 349-355, vol. 163.
Akbiyik et al., "In vitro and in vivo inhibition of myeloperoxidase with 5-fluorouracil," Eur. J. Clin. Pharmacol., 2001, vol. 57, pp. 631-636.
Albert et al., "Reactive Chlorinating Species Produced by Myeloperoxidase Target the Vinyl Ether Bond of Plasmalogans," J. Biol. Chem., 2001, vol. 276(26), pp. 23733-23741.
Armitage et al., "Structure-Activity Relationships in a Series of 6-Thioxanthines with Bronchodilator and Coronary Dilator Properties," British Journal of Pharmacology and Chemotherapy (1961), vol. 17, pp. 196-207.

Asselbergs et al., "Myeloperoxidase Polymorphism Related to Cardiovascular Events in Coronary Artery Disease," (2004) Am J Med 116(6): 429-30.
Baldus, S. et al., "Myeloperoxidase Serum Levels Predict Risk in Patients with Acute Coronary Syndromes," Circulation, 2003, pp. 1440-1445, vol. 108.
Bergt et al., "The Myeloperoxidase Product Hypochlorous Acid Oxidizes HDL in the Human Artery Wall and Impairs ABCA1-Dependent Cholesterol Transport," Proc Natl Acad Sci, 2004, vol. 101(35), pp. 13032-13037.
Bergt et al., "Lysine Residues Direct the Chlorination of Tyrosines in YXXK Motifs of Apolipoprotein A-I When Hypochlorous Acid Oxidizes High Density Lipoprotein," (2004) J Biol Chem 279(9): 7856-66.
Berlow et al., "The Effect of Dapsone in Steroid-Dependent Asthma," 1991, J. Allergy Clin. Immunol., 1991, vol. 87 (3), pp. 710-715.
Bozeman et al., "Inhibition of the human leukocyte enzymes myeloperoxidase and eosinophil peroxidase by dapsone," Biochemical Pharmacology, 1992, vol. 44, No. 3, pp. 553-563.
Brennan, M. et al., "Prognostic Value of Myeloperoxidase in Patients with Chest Pain," N Engl J Med., 2003, pp. 1595-1604, vol. 349, No. 17.
Choi, D-K et al., "Ablation of the Inflammatory Enzyme Myeloperoxidase Mitigates Features of Parkinson's Disease in Mice," J. Neurosci., 2005, pp. 6594-6600, vol. 25, No. 28.
Crooks, S W et al., "Bronchial Inflammation in Acute Bacterial Exacerbations of Chronic Bronchitis: the Role of Leukotriene B4," European Respiratory Journal, 2000, pp. 274-280, vol. 15, No. 2.
Cuzner, M L et al., "Plasminogen Activators and Matrix Metalloproteases, Mediators of Extracellular Proteolysis in Inflammatory Demyelination of the Central Nervous System," Journal of Neuroimmunology, 1999, pp. 1-14, vol. 94, No. 1-2.
Dallegri et al., "Possible Modes of Action of Nimesulide in Controlling Neutrophilic Inflammation," Arzneimittel-Foschung/Drug Research, 1995, vol. 45(II), No. 10, pp. 1114-1117.
Daugherty, A. et al., "Myeloperoxidase, a Catalyst for Lipoprotein Oxidation, Is Expressed in Human Atherosclerotic Lesions," J Clin Invest., 1994, pp. 437-444, vol. 94, No. 1.
Fiorini, G. et al., "Serum ECP and MPO are Increased During Exacerbations of Chronic Bronchitis with Airway Obstruction," Biomedicine & Pharmacotherapy, 2000, pp. 274-278, vol. 54.
Fu et al., "Generation of Intramolecular and Intermolecular Sulfenamides, Sulfinamides, and Sulfonamides by Hypochlorous Acid: A Potential Pathway for Oxidative Cross-Linking of Low-Density Lipoprotein by Myeloperoxidase," Biochemistry 2002; 41(4):1293-1301.
Fu et al., "Hypochlorous Acid Oxygenates the Cysteine Switch Domain of Pro-matrilysin (MMP-7)," J. Biol. Chem. 2001; 276(44):41279-41287.
Furneaux et al., "Improved Syntheses of 3H,5H-Pyrrolo[3,2-d]pyrimidines," J. Org. Chem. 1999, vol. 64, pp. 8411-8412.
Garst et al., "Inhibition of Separated Forms of Phosphodiesterases from Pig Coronary Arteries by Uracils and by 7-Substituted Derivatives of 1-Methyl-3-isobutylxanthine," J. Med. Chem.; 1976; vol. 19(4) pp. 499-503.
Green, P S et al., "Neuronal Expression of Myeloperoxidase is Increased in Alzheimer's Disease," Journal of Neurochemistry, 2004, pp. 724-733, vol. 90, No. 3.
Grisham et al., "Assessment of Leukocye involvement during Ischemia and Reperfusion of Intestine," Am. J. Physiol., 1986, vol. 251, pp. 729-743.
Gu et al., "S-Nitrosylation of Matrix Metalloproteinases: Signaling Pathway to Neuronal Cell Death," Science, 2002; vol. 297(5584), pp. 1186-1190.
Hale et al., "Morphologic Changes in the Muscular Pulmonary Arteries: Relationship to Cigarette Smoking, Airway Disease, and Emphysema," American Review of Respiratory Disease, 1980, vol. 122, pp. 273-278.
Hampton, M B, et al., "Inside the Neutrophil Phagosome: Oxidants, Myeloperoxidase, and Bacterial Killing," Blood, 1998, pp. 3007-3017, vol. 92, No. 9.
Hazell et al., "Oxidation of Low-Density Lipoprotein with Hypochlorite Causes Transformation of the Lipoprotein into a High-Uptake Form for Macrophages," Biochemical Journal, 1993, vol. 290 (Pt 1): pp. 165-172.
Hazen et al., "Mass Spectrometric Quantification of 3-Chlorotyrosine in Human Tissues with Attomole Sensitivity: A Sensitive and Specific Marker for Myeloperoxidase-Catalyzed Chlorination at Sites of Inflammation," Free Radical Biology and Medicine, 1997, vol. 23(6), pp. 909-916.
Hazen et al., "3-Chlorotyrosine, a Specific Marker of Myeloperoxidase-catalyzed Oxidation, Is Markedly Elevated in Low Density Lipoprotein Isolated from Human Atherosclerotic Intima," Journal of Clinical Investigation, 1997, vol. 99(9), pp. 2075-2081.
Hope et al., "Large scale purification of myeloperoxidase from HL60 promyelocytic cells: characterization and comparison to human neutrophil myeloperoxidase," Protein Expression and Purification, 2000, vol. 18, pp. 269-276.
Imai et al., "Studies on Nucleic Acid Antagonists. VII. Synthesis and Characterization of 1,4,6-Triazaindenes (5H-Pyrrolo(3,2-d)pyrimidines)" Chem. Pharm. Bull., 1964, vol. 12, No. 9, pp. 1030-1042.
Jacobson et al., "1,3-Dialkylxanthine Derivatives Having High Potency as Antagonists at Human A2B Adenosine Receptors," Drug Development Research, 1999, vol. 47, pp. 45-53.
Keatings et al., "Granulocyte Activation Markers in Induced Sputum: Comparison Between Chronic Obstructive Pulmonary Disease, Asthma, and Normal Subjects," American Journal of Respiratory and Critical Care Medicine, 1997, vol. 155, pp. 449-453.
Kettle et al., "Assays for the Chlorination Activity of Myeloperoxidase," Biophyl, 1992, vol. 296, pp. 502-513.
Kettle et al., "Mechanism of inhibition of myeloperoxidase by antiinflammatory drugs," Biochemical Pharmacology, 1991, vol. 41, No. 10, pp. 1485-1492.
Kettle et al., "Superoxide is an Antagonist of Anti-Inflammatory Drugs that Inhibit Hyposchlorous Acid Production by Myeloperoxidase," Biochemical Pharmacology, 1993, vol. 45, No. 10, pp. 2003-2010.
Khimicheskaya encyclopedia, ed. by Knunyants I.L., "Sovetskaya encyclopedia", 1990, V. 2, p. 1083.
Kolasa et al., "Reactions of Alpha-Hydroxy Carbonyl Compounds With Azodicarboxylates and Triphenylphosphine: Synthesis of Alpha-N-Hydroxy Amino Acid Derivatives," Journal of Organic Chemistry, 1987, vol. 52, pp. 4978-4984.
Kutter, D. et al., "Consequences of Total and Subtotal Myeloperoxidase Deficiency: Risk or Benefit?," Acta Haematol, 2000, pp. 10-15, vol. 104, No. 1.
Lassmann, "Axonal Injury in Multiple Sclerosis," J Neurol Neurosurg Psychiatry, 2003, vol. 74(6), pp. 695-697.
Leckie et al., "Novel Therapy for COPD," Exp. Opin. Invest. Drugs, 2000, vol. 9(1), pp. 3-23.
Makela et al., "Myeloperoxidase Gene Variation as a Determinant of Atherosclerosis Progression in the Abdominal and Thoracic Aorta: An Autopsy Study," Laboratory Investigation, 2003, vol. 83(7), pp. 919-925.
Martin et al., "Reduction of Neutrophil-mediated injury to pulmonary endothelial cells by Dapsone 1-3", Am. Rev. Respir Dis., 1985, vol. 131, pp. 544-547.
Nagra, R M, et al., "Immunohistochemical and Genetic Evidence of Myeloperoxidase Involvement in Multiple Sclerosis," Journal of Neuroimmunology, 1997, pp. 97-107, vol. 78, No. 1-2.
Nicholls et al., "Myeloperoxidase and Cardiovascular Disease," Arterioscler Thromb Vasc Biol, 2005, vol. 25(6), pp. 1102-1111.
Nikpoor et al., "A Functional Myeloperoxidase Polymorphic Variant is Associated with Coronary Artery Disease in French-Canadians," American Heart Journal, 2001, vol. 142, p. 336-339.
Nocker et al., "Interleukin-8 in Airway Inflammation in Patients with Chronic Asthma and Chronic Obstructive Pulmonary Disease," Int. Arch Allergy Immunol., 1996, vol. 109, pp. 183-191.
Norman et al., "Structure-Activity Relationships of a Series of Pyrrolo[3,2-d]pyrimidine Derivatives and Related Compounds as Neuropeptide Y5 Receptor Antagonists," Journal of Medicinal Chemistry, 2000, vol. 43, pp. 4288-4312.
Ottonello et al., "Sulphonamides as Anti-Inflammatory Agents: Old Drugs for New Therapeutic Strategies in Neutrophilic Inflammation," Clinical Science, 1995, vol. 88, pp. 331-336.

* cited by examiner

PYRROLO [3,2-D]PYRIMIDIN-4-ONE DERIVATIVES AND THEIR USE IN THERAPY

CROSS REFERENCE TO RELATED APPLICATIONS

This application is a US National Stage under 35 USC section 371 of International Application No. PCT/SE2005/001835, Filed Dec. 5, 2005, which claims priority under 35 USC sections 119 (a)-(d) to Swedish Application Nos. 0402972 filed on Dec. 6, 2004 and 0501093-9 filed on May 13, 2005.

FIELD OF THE INVENTION

The present invention relates to novel pyrrolo[3,2-d]pyrimidin-4-one derivatives, processes for their preparation, compositions containing them and their use in therapy.

BACKGROUND OF THE INVENTION

Myeloperoxidase (MPO) is a heme-containing enzyme found predominantly in polymorphonuclear leukocytes (PMNs). MPO is one member of a diverse protein family of mammalian peroxidases that also includes eosinophil peroxidase, thyroid peroxidase, salivary peroxidase, lactoperoxidase, prostaglandin H synthase, and others. The mature enzyme is a dimer of identical halves. Each half molecule contains a covalently bound heme that exhibits unusual spectral properties responsible for the characteristic green colour of MPO. Cleavage of the disulphide bridge linking the two halves of MPO yields the hemi-enzyme that exhibits spectral and catalytic properties indistinguishable from those of the intact enzyme. The enzyme uses hydrogen peroxide to oxidize chloride to hypochlorous acid. Other halides and pseudohalides (like thiocyanate) are also physiological substrates to MPO.

PMNs are of particular importance for combating infections. These cells contain MPO, with well documented microbicidal action. PMNs act non-specifically by phagocytosis to engulf microorganisms, incorporate them into vacuoles, termed phagosomes, which fuse with granules containing myeloperoxidase to form phagolysosomes. In phagolysosomes the enzymatic activity of the myeloperoxidase leads to the formation of hypochlorous acid, a potent bactericidal compound. Hypochlorous acid is oxidizing in itself, and reacts most avidly with thiols and thioethers, but also converts amines into chloramines, and chlorinates aromatic amino acids. Macrophages are large phagocytic cells which, like PMNs, are capable of phagocytosing microorganisms. Macrophages can generate hydrogen peroxide and upon activation also produce myeloperoxidase. MPO and hydrogen peroxide can also be released to the outside of the cells where the reaction with chloride can induce damage to adjacent tissue.

Linkage of myeloperoxidase activity to disease has been implicated in neurological diseases with a neuroinflammatory response including multiple sclerosis, Alzheimer's disease, Parkinson's disease and stroke as well as other inflammatory diseases or conditions like asthma, chronic obstructive pulmonary disease, cystic fibrosis, atherosclerosis, inflammatory bowel disease, renal glomerular damage and rheumatoid arthritis. Lung cancer has also been suggested to be associated with high MPO levels.

Multiple Sclerosis (MS)

MPO positive cells are immensely present in the circulation and in tissue undergoing inflammation. More specifically MPO containing macrophages and microglia has been documented in the CNS during disease; multiple sclerosis (Nagra R M, et al. Journal of Neuroimmunology 1997; 78(1-2):97-107), Parkinson's disease (Choi D-K. et al. J. Neurosci. 2005; 25(28):6594-600) and Alzheimer's disease (Green P S. et al. Journal of Neurochemistry. 2004; 90(3):724-33). It is supposed that some aspects of a chronic ongoing inflammation result in an overwhelming destruction where agents from MPO reactions have an important role.

The enzyme is released both extracellularly as well as into phagolysosomes in the neutrophils (Hampton M B, Kettle A J, Winterbourn C C. Blood 1998; 92(9):3007-17). A prerequisite for the MPO activity is the presence of hydrogen peroxide, generated by NADPH oxidase and a subsequent superoxide dismutation. The oxidized enzyme is capable to use a plethora of different substrates of which chloride is most recognized. From this reaction the strong non-radical oxidant—hypochlorous acid (HOCl)—is formed. HOCl oxidizes sulphur containing amino acids like cysteine and methionine very efficiently (Peskin A V, Winterbourn C C. Free Radical Biology and Medicine 2001; 30(5):572-9). It also forms chloramines with amino groups, both in proteins and other biomolecules (Peskin A V. et al. Free Radical Biology and Medicine 2004; 37(10):1622-30). It chlorinates phenols (like tyrosine) (Hazen S L. et al. Mass Free Radical Biology and Medicine 1997; 23(6):909-16) and unsaturated bonds in lipids (Albert C J. et al. J. Biol. Chem. 2001; 276 (26):23733-41), oxidizes iron centers (Rosen H, Klebanoff S J. Journal of Biological Chemistry 1982; 257(22):13731-354) and crosslinks proteins (Fu X, Mueller D M, Heinecke J W. Biochemistry 2002; 41(4):1293-301).

Proteolytic cascades participate both in cell infiltration through the BBB as well as the destruction of BBB, myelin and nerve cells (Cuzner M L, Opdenakker G. Journal of Neuroimmunology 1999; 94(1-2):1-14; Yong V W. et al. Nature Reviews Neuroscience 2001; 2(7):502-11.). Activation of matrix metalloproteinases (MMPs) can be accomplished through the action of upstream proteases in a cascade as well as through oxidation of a disulfide bridge Fu X. et al. J. Biol. Chem. 2001; 276(44):41279-87; Gu Z. et al. Science 2002; 297(5584):1186-90). This oxidation can be either a nitrosylation or HOCl-mediated oxidation. Both reactions can be a consequence of MPO activity. Several reports have suggested a role for MMP's in general and MMP-9 in particular as influencing cell infiltration as well as tissue damage (BBB breakdown and demyelination), both in MS and EAE (for review see Yong V W. et al, supra). The importance of these specific kinds of mechanisms in MS comes from studies where increased activity and presence of proteases have been identified in MS brain tissue and CSF. Supportive data has also been generated by doing EAE studies with mice deficient in some of the proteases implicated to participate in the MS pathology, or by using pharmacological approaches.

The demyelination is supposed to be dependent on the cytotoxic T-cells and toxic products generated by activated phagocytes (Lassmann H. J Neurol Neurosurg Psychiatry 2003; 74(6):695-7). The axonal loss is thus influenced by proteases and reactive oxygen and nitrogen intermediates. When MPO is present it will obviously have the capability of both activating proteases (directly as well as through disinhibition by influencing protease inhibitors) and generating reactive species.

Chronic Obstructive Pulmonary Disease (COPD)

Chronic obstructive pulmonary disease (COPD) is a disease state characterised by airflow limitation that is not fully reversible. The airflow limitation is usually both progressive and associated with an abnormal inflammatory response of the lungs to noxious particles or gases. COPD is a major public health problem. It is the fourth leading cause of chronic morbidity and mortality in the United States1 and is projected to rank fifth in 2020 as a worldwide burden of disease. In the UK the prevalence of COPD is 1.7% in men and 1.4% in women. COPD spans a range of severity from mild to very severe, with the cost of treatment rising rapidly as the severity increases.

Levels of MPO in sputum and BAL are much greater in COPD patients that normal, non-smoking controls (Keatings V. M., Barnes P. J. Am J Respir Crit Care Med 1997; 155: 449-453; Pesci, A. et al. Eur Respir J 1998; 12:380-386). MPO levels are further elevated during exacerbations of the disease (Fiorini G. et al. Biomedicine & Pharmacotherapy 2000; 54: 274-278; Crooks S. W. et al. European Respiratory Journal. 15(2):274-80, 2000). The role of MPO is likely to be more important in exacerbations of COPD (Sharon S. D. et al. Am J Respir Crit Care Med. 2001; 163:349-355).

In addition to the destructive capacity of MPO there is a strong clinical link with vascular disease (Baldus S. et al. Circulation 2003; 108:1440-5). Dysfunctional MPO polymorphisms are associated with a reduced risk of mortality from coronary artery disease (Nikpoor B. et al. Am Heart J 2001; 142:336), and patients with high serum levels of MPO have increased risk of acute coronary syndrome. The effects of MPO on vascular disease may extend to COPD, since there is strong evidence that the pulmonary vasculature is one of the earliest sites of involvement in the smokers' lung. Striking changes in the intima of the pulmonary arteries have been described which show a dose relationship with smoking (Hale K. A., Niewoehner D. E., Cosio M. G. Am Rev Resp Dis 1980; 122:273-8). The physiological function of MPO is associated with innate host defence. This role, however, is not critical as most cases of MPO deficient patients have relatively benign symptoms (Parry M. F. et al. Ann Int Med. 1981; 95:293-301, Yang, K. D., Hill, H. R. Pediatr Infect Dis J. 2001; 20: 889-900). In summary, there is considerable evidence that elevated MPO levels in COPD may contribute to the disease via several mechanisms. A selective inhibitor of MPO would therefore be expected to alleviate both the acute and chronic inflammatory aspects of COPD and may reduce the development of emphysema.

Atherosclerosis

An MPO inhibitor should reduce the atherosclerotic burden and/or the vulnerability of existing atherosclerotic lesions and thereby decrease the risk of acute myocardial infarction, unstable angina or stroke. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al. (1994) J Clin Invest 94(1): 437-44). In eroded and ruptured human lesions, as compared to fatty streaks, an increased number of MPO expressing macrophages have been demonstrated, suggesting a particular role for MPO in acute coronary syndromes (Sugiyama, S. et al. (2001) Am J Pathol 158(3): 879-91). Patients with established coronary artery disease have higher plasma and leukocyte MPO levels than healthy controls (Zhang, R. et al. (2001) Jama 286(17): 2136-42). Moreover, in two large prospective studies plasma levels of MPO predicted the risk of future coronary events or revascularisation (Baldus, S. et al. (2003) Circulation 108(12): 1440-5; Brennan, M. et al. (2003) N Engl J Med 349(17): 1595-604). Total MPO deficiency in humans has a prevalece of 1 in 2000-4000 individuals. These individuals appear principally healthy but a few cases of severe *Candida* infection have been reported. Interestingly, MPO deficient humans are less affected by cardiovascular disease than controls with normal MPO levels (Kutter, D. et al. (2000) Acta Haematol 104(1)). A polymorphism in the MPO promoter affects expression leading to high and low MPO expressing individuals. In three different studies the high expression genotype has been associated with an increased risk of cardiovascular disease (Nikpoor, B. et al. (2001) Am Heart J 142(2): 336-9; Makela, R., P. J. Karhunen, et al. (2003) Lab Invest 83(7): 919-25; Asselbergs, F. W., et al. (2004) Am J Med 116(6): 429-30). Data accumulated during the last ten years indicate that the proatherogenic actions of MPO include oxidation of lipoproteins, induction of endothelial dysfunction via consuming nitric oxide and destabilisation of atherosclerotic lesions by activation of proteases (Nicholls, S. J. and S. L. Hazen (2005) Arterioscler Thromb Vasc Biol 25(6): 1102-11). Recently, several studies have focused on nitro- and chlorotyrosine modifications of LDL and HDL lipoproteins. Since chlorotyrosine modifications in vivo only can be generated by hypochlorous acid produced by MPO these modifications are regarded as specific markers of MPO activity (Hazen, S. L. and J. W. Heinecke (1997) J Clin Invest 99(9): 2075-81). LDL particles exposed to MPO in vitro become aggregated, leading to facilitated uptake via macrophage scavenger receptors and foam cell formation (Hazell, L. J. and R. Stocker (1993) Biochem J 290 (Pt 1): 165-72). Chlorotyrosine modification of apoA1, the main apolipoprotein of HDL cholesterol, results in impaired cholesterol acceptor function (Bergt, C., S. et al. (2004) Proc Natl Acad Sci USA; Zheng, L. et al. (2004) J Clin Invest 114(4): 529-41). Systematic studies of these mechanisms have shown that MPO binds to and travels with apoA1 in plasma. Moreover, MPO specifically targets those tyrosine residues of apoA1 that physically interact with the macrophage ABCA1 cassette transporter during cholesterol efflux from the macrophage (Bergt, C. et al. (2004) J Biol Chem 279(9): 7856-66; Shao, B. et al. (2005) J Biol Chem 280(7): 5983-93; Zheng et al. (2005) J Biol Chem 280(1): 38-47). Thus, MPO seems to have a dual aggravating role in atherosclerotic lesions, i.e. increasing lipid accumulation via aggregation of LDL particles and decreasing the reverse cholesterol transport via attack on the HDL protein apoA1.

1-β-D-Ribofuranosyl-2-oxopyrrolo[3,2-d]pyrimidine-4 (3H,5H)-thione and 1-(2,3,5-tri-O-benzoyl-1-β-D-ribofuranosyl)-2-oxopyrrolo[3,2-d]pyrimidine-4(3H,5H)-thione

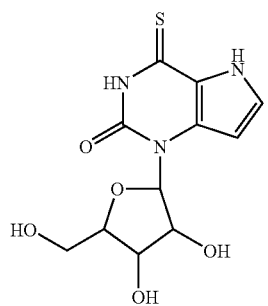

-continued

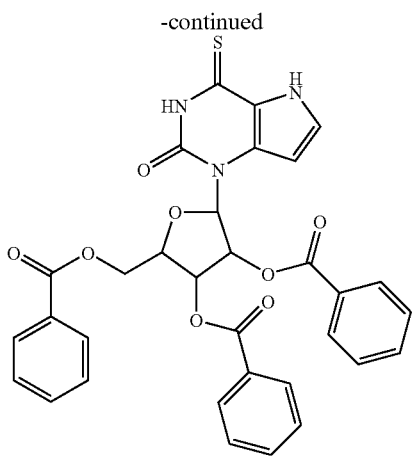

are disclosed in J. Heterocyclic Chemistry, 1992, 29, 343-354. No pharmacological activity is ascribed to these compounds.

5,7-Dimercapto-1,4,6-triazaindene

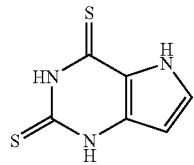

is disclosed in Chem. Pharm. Bull., 1964, 12, 1030-1042 and in Japanese patent JP 02160235 A2. No pharmacological activity is ascribed to this compound.

The present invention discloses novel pyrrolo[3,2-d]pyrimidin-4-one derivatives that surprisingly display useful properties as inhibitors of the enzyme MPO. These compounds may also show selectivity against related enzymes e.g. lactoperoxidase (LPO) and thyroidperoxidase (TPO).

DISCLOSURE OF THE INVENTION

The present invention provides compounds of formula (I)

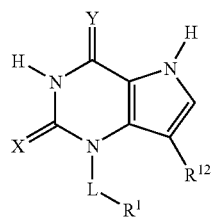

(I)

wherein:

at least one of X and Y represents S, and the other represents O or S;

L represents a direct bond or C1 to 7 alkylene, said alkylene optionally incorporating a heteroatom selected from O, $S(O)_n$ and $NR^6$, said alkylene optionally incorporating one or two carbon-carbon double bonds, and said alkylene being optionally substituted by one or more substituents selected independently from OH, halogen, CN and $NR^4R^5$, C1 to 6 alkyl and C1 to 6 alkoxy, said alkoxy optionally incorporating a carbonyl adjacent to the oxygen;

n represents an integer 0, 1 or 2;

$R^1$ represents hydrogen, or i) a saturated or partially unsaturated 3 to 7 membered ring optionally incorporating one or two heteroatoms selected independently from O, N and S, and optionally incorporating a carbonyl group, optionally substituted by one or more substituents independently selected from halogen, $SO_2R^9$, $SO_2NR^9R^{10}$, OH, C1 to 7 alkyl, C1 to 7 alkoxy, CN, $CONR^2R^3$, $NR^2COR^3$ and $COR^3$, said alkoxy being optionally further substituted by C1 to 6 alkoxy and said alkoxy optionally incorporating a carbonyl adjacent to the oxygen, and said alkyl being optionally further substituted by hydroxy or C1 to 6 alkoxy and said alkyl or alkoxy optionally incorporating a carbonyl adjacent to the oxygen or at any position in the alkyl; or ii) an aromatic ring system selected from phenyl, biphenyl, naphthyl or a monocyclic or bicyclic heteroaromatic ring structure containing 1 to 3 heteroatoms independently selected from O, N and S, said aromatic ring system being optionally substituted by one or more substituents independently selected from halogen, $SO_2R^9$, $SO_2NR^9R^{10}$, OH, C1 to 7 alkyl, C1 to 7 alkoxy, CN, $CONR^2R^3$, $NR^2COR^3$ and $COR^3$; said alkoxy being optionally further substituted by C1 to 6 alkoxy and said alkoxy optionally incorporating a carbonyl adjacent to the oxygen, and said alkyl being optionally further substituted by hydroxy or C1 to 6 alkoxy and said alkyl or alkoxy optionally incorporating a carbonyl adjacent to the oxygen or at any position in the alkyl;

$R^{12}$ represents hydrogen or halogen or a carbon optionally substituted with one to three halogen atoms;

at each occurrence, $R^2$, $R^3$, $R^4$, $R^5$, $R^6$, $R^9$ and $R^{10}$ independently represent hydrogen, C1 to 6 alkyl or C1 to 6 alkoxy said alkoxy optionally incorporating a carbonyl adjacent to the oxygen, said alkyl being optionally further substituted by halogen, C1 to 6 alkoxy, CHO, C2 to 6 alkanoyl, OH, $CONR^7R^8$ and $NR^7COR^8$;

or the groups $NR^2R^3$, $NR^4R^5$ and $NR^9R^{10}$ each independently represent a 5 to 7 membered saturated azacyclic ring optionally incorporating one additional heteroatom selected from O, S and $NR^{11}$, said ring being optionally further substituted by halogen, C1 to 6 alkoxy, CHO, C2 to 6 alkanoyl, OH, $CONR^7R^8$ and $NR^7COR^8$;

at each occurrence $R^7$, $R^8$ and $R^{11}$ independently represent hydrogen or C1 to 6 alkyl, or the group $NR^7R^8$ represents a 5- to 7-membered saturated azacyclic ring optionally incorporating one additional heteroatom selected from O, S and $NR^{11}$;

and pharmaceutically acceptable salts thereof;

with the proviso that the compounds 1-β-D-ribofuranosyl-2-oxopyrrolo[3,2-d]pyrimidine-4(3H,5H)-thione, 1-(2,3,5-tri-O-benzoyl-1-β-D-ribofuranosyl)-2-oxopyrrolo[3,2-d]pyrimidine-4(3H,5H)-thione and 5,7-dimercapto-1,4,6-triazaindene are disclaimed.

The compounds of formula (I) may exist in enantiomeric forms. It is to be understood that all enantiomers, diastereomers, racemates, tautomers and mixtures thereof are included within the scope of the invention.

The compounds of formula (I) may exist in tautomeric forms. All such tautomers and mixtures of tautomers are included within the scope of the present invention.

Unless otherwise indicated, the term "C1 to 6 alkyl" referred to herein denotes a straight or branched chain alkyl group having from 1 to 6 carbon atoms. Examples of such groups include, but are not limited to, methyl, ethyl, 1-propyl, n-butyl, iso-butyl, tert-butyl, pentyl and hexyl. The term "C1 to 7 alkyl" is to be interpreted analogously Unless otherwise indicated, the term "C1 to 7 alkylene" referred to herein denotes a straight or branched chain alkyl group having from 1 to 7 carbon atoms having two free valencies. Examples of such groups include, but are not limited to, methylene, ethylene, propylene, hexamethylene and ethylethylene. The term "C1 to 3 alkylene" is to be interpreted analogously.

Unless otherwise indicated, the term "C1 to 6 alkoxy" referred to herein denotes a straight or branched chain alkoxy group having from 1 to 6 carbon atoms. Examples of such groups include, but are not limited to, methoxy, ethoxy, 1-propoxy, 2-propoxy(iso-propoxy), tert-butoxy and pentoxy. The term "C1 to 7 alkoxy" is to be interpreted analogously.

Unless otherwise indicated, the term "C2 to 6 alkanoyl" referred to herein denotes a straight or branched chain alkyl group having from 1 to 5 carbon atoms with optional position on the alkyl group by a carbonyl group. Examples of such groups include, but are not limited to, acetyl, propionyl and pivaloyl.

Unless otherwise indicated, the term "halogen" referred to herein denotes fluoro, chloro, bromo and iodo.

Examples of a saturated or partially unsaturated 3- to 7-membered ring optionally incorporating one or two heteroatoms selected independently from O, N and S, and optionally incorporating a carbonyl group includes, but is not limited to, cyclopropane, cyclopentane, cyclohexane, cyclohexene, cyclopentanone, tetrahydrofuran, pyrrolidine, piperidine, tetrahydropyridine, morpholine, piperazine, pyrrolidinone and piperidinone.

Examples of a monocyclic or bicyclic heteroaromatic ring structure containing 1 to 3 heteroatoms independently selected from O, N and S includes, but is not limited to, furan, thiophene, pyrrole, oxazole, isoxazole, thiazole, imidazole, pyrazole, triazole, tetrazole, pyridine, pyrazine, pyrimidine, pyridazine, benzofuran, indole, isoindole and benzimidazole.

Examples of a 5 to 7 membered saturated azacyclic ring optionally incorporating one additional heteroatom selected from O, S and $NR^{11}$ includes, but is not limited to, pyrrolidine, piperidine, piperazine, morpholine and thiomorpholine.

In the definition of L, "C1 to 7 alkylene; said alkylene optionally incorporating a heteroatom selected from O, $S(O)_n$ and $NR^6$; said alkylene optionally incorporating one or two carbon-carbon double bonds" embraces a saturated or unsaturated straight or branched chain arrangement of 1 to 7 carbon atoms having two free valencies and in which any two singly bonded carbon atoms are optionally separated by O, S or $NR^6$. The definition thus includes, for example, methylene, ethylene, propylene, hexamethylene, ethylethylene, —CH$_2$=CH$_2$—, —CH$_2$CH=CH—CH$_2$—, —CH(CH$_3$)=CH$_2$—, —CH$_2$=CH$_2$—CH$_2$O—, —CH$_2$O—, —CH$_2$CH$_2$O—CH$_2$—, —CH$_2$CH$_2$O—CH$_2$—CH$_2$—, —CH$_2$CH$_2$S— and —CH$_2$CH$_2$NR$^6$—.

In one embodiment, $R^1$ represents hydrogen.

In another embodiment, X represents S and Y represents O.

In yet another embodiment, Y represents S and X represents O.

In yet another embodiment, L is a direct bond or represents C1 to 7 alkylene, said alkylene optionally incorporating a heteroatom selected from O, $S(O)_n$ and $NR^6$, said alkylene optionally incorporating one or two carbon-carbon double bonds, and said alkylene being optionally substituted by one or more substituents selected independently from OH, C1 to 6 alkoxy, halogen, CN and $NR^4R^5$.

In yet another embodiment, L is a direct bond or represents C1 to 7 alkylene; said alkylene being optionally substituted by one or more substituents selected independently from OH, C1 to 6 alkoxy, halogen, CN and $NR^4R^5$.

In yet another embodiment, L is a direct bond or represents C1 to 7 alkylene; said alkylene being optionally substituted by one or more C1 to 6 alkoxy.

In yet another embodiment, L is a direct bond or represents C1 to 3 alkylene; said alkylene being optionally substituted by one or more substituents selected independently from OH, C1 to 6 alkoxy, halogen, CN and $NR^4R^5$.

In yet another embodiment, L represents C1 to 3 alkylene; said alkylene being optionally substituted by one or more C1 to 6 alkoxy.

In yet another embodiment, L is a direct bond or represents optionally substituted methylene (—CH$_2$—).

In yet another embodiment, L is a direct bond or represents optionally substituted ethylene (—CH$_2$CH$_2$—).

In yet another embodiment, $R^1$ represents a saturated or partially unsaturated 3 to 7 membered ring optionally incorporating one or two heteroatoms selected independently from O, N and S, and optionally incorporating a carbonyl group, said ring being optionally substituted by one or more substituents independently selected from halogen, $SO_2R^9$, $SO_2NR^9R^{10}$, OH, C1 to 6 alkyl, C1 to 6 alkoxy, CN, $CONR^2R^3$, $NR^2COR^3$ and $COR^3$, said alkoxy being optionally further substituted by C1 to 6 alkoxy; and said alkyl being optionally further substituted by hydroxy or C1 to 6 alkoxy.

In yet another embodiment, $R^1$ represents a saturated or partially unsaturated 3 to 7 membered ring optionally incorporating one or two heteroatoms selected independently from O, N and S, and optionally incorporating a carbonyl group; said ring being optionally substituted by one or more substituents independently selected from halogen, C1 to 6 alkyl and C1 to 6 alkoxy, said alkoxy being optionally further substituted by C1 to 6 alkoxy.

In yet another embodiment, $R^1$ represents an aromatic ring system selected from phenyl, biphenyl, naphthyl or a monocyclic or bicyclic heteroaromatic ring structure containing 1 to 3 heteroatoms independently selected from O, N and S, said aromatic ring being optionally substituted by one or more substituents independently selected from halogen, $SO_2R^9$, $SO_2NR^9R^{10}$, OH, C1 to 6 alkyl, C1 to 6 alkoxy, CN, $CONR^2R^3$, $NR^2COR^3$ and $COR^3$, said alkoxy being optionally further substituted by C1 to 6 alkoxy, and said alkyl being optionally further substituted by hydroxy or C1 to 6 alkoxy.

In yet another embodiment, $R^1$ represents an aromatic ring system selected from phenyl, biphenyl, naphthyl or a five- or six-membered heteroaromatic ring containing 1 to 3 heteroatoms independently selected from O, N and S, said aromatic ring being optionally substituted by one or more substituents independently selected from halogen, C1 to 6 alkyl and C1 to 6 alkoxy, said alkoxy being optionally further substituted by C1 to 6 alkoxy.

In yet another embodiment, $R^1$ represents an optionally substituted phenyl.

In yet another embodiment, $R^1$ represents an optionally substituted pyridyl.

In yet another embodiment, L represents C1 to 7 alkylene and $R^1$ represents H.

In yet another embodiment, L represents an optionally substituted C1 to 3 alkylene and $R^1$ represents a saturated or partially unsaturated 3- to 7-membered ring optionally incorporating one or two heteroatoms selected independently from O, N and S, and optionally incorporating a carbonyl group, said ring being optionally substituted by one or more substituents independently selected from halogen, $SO_2R^9$, $SO_2NR^9R^{10}$, OH, C1 to 6 alkyl, C1 to 6 alkoxy, CN, $CONR^2R^3$, $NR^2COR^3$ and $COR^3$, said alkoxy being optionally further substituted by C1 to 6 alkoxy, and said alkyl being optionally further substituted by hydroxy or C1 to 6 alkoxy.

In yet another embodiment, L represents an optionally substituted C1 to 3 alkylene and $R^1$ represents a saturated or partially unsaturated 3- to 7-membered ring optionally incorporating one or two heteroatoms selected independently from O, N and S, and optionally incorporating a carbonyl group, said ring being optionally substituted by one or more substituents independently selected from halogen, C1 to 6 alkyl and C1 to 6 alkoxy, said alkoxy being optionally further substituted by C1 to 6 alkoxy.

In yet another embodiment, L represents optionally substituted C1 to 3 alkylene and $R^1$ represents an aromatic ring system selected from phenyl, biphenyl, naphthyl or a five- or six-membered heteroaromatic ring containing 1 to 3 heteroatoms independently selected from O, N and S; said aromatic ring being optionally substituted by one or more substituents independently selected from halogen, $SO_2R^9$, $SO_2NR^9R^{10}$, OH, C1 to 6 alkyl, C1 to 6 alkoxy, CN, $CONR^2R^3$, $NR^2COR^3$ and $COR^3$, said alkoxy being optionally further substituted by C1 to 6 alkoxy, and said alkyl being optionally further substituted by hydroxy or C1 to 6 alkoxy.

In yet another embodiment, L represents optionally substituted C1 to 3 alkylene and $R^1$ represents an aromatic ring system selected from phenyl, biphenyl, naphthyl or a five- or six-membered heteroaromatic ring containing 1 to 3 heteroatoms independently selected from O, N and S, said aromatic ring being optionally substituted by one or more substituents independently selected from halogen, C1 to 6 alkyl and C1 to 6 alkoxy, said alkoxy being optionally further substituted by C1 to 6 alkoxy.

In yet another embodiment, X represents S, Y represents O, L represents optionally substituted C1 to 3 alkylene and $R^1$ represents optionally substituted phenyl.

In yet another embodiment, X represents S, Y represents O, L represents optionally substituted C1 to 3 alkylene and $R^1$ represents optionally substituted pyridyl.

In yet another embodiment, X represents S, Y represents O, L represents C1 to 3 alkylene, substituted with C1 to 6 alkoxy and $R^1$ represents hydrogen.

Particular compounds of the invention include:
1-butyl-2-thioxo-1,2,3,5-tetrahydro-pyrrolo[3,2-d]pyrimidin-4-one;
1-isobutyl-2-thioxo-1,2,3,5-tetrahydro-pyrrolo[3,2-d]pyrimidin-4-one;
1-(pyridin-2-ylmethyl)-2-thioxo-1,2,3,5-tetrahydro-pyrrolo[3,2-d]pyrimidin-4-one;
1-(2-fluoro-benzyl)-2-thioxo-1,2,3,5-tetrahydro-pyrrolo[3,2-d]pyrimidin-4-one;
1-[2-(2-methoxyethoxy)-3-propoxybenzyl]-2-thioxo-1,2,3,5-tetrahydro-pyrrolo[3,2-d]pyrimidin-4-one;
1-(6-ethoxy-pyridin-2-ylmethyl)-2-thioxo-1,2,3,5-tetrahydro-pyrrolo[3,2-d]pyrimidin-4-one;
1-piperidin-3-ylmethyl-2-thioxo-1,2,3,5-tetrahydro-pyrrolo[3,2-d]pyrimidin-4-one;
1-butyl-4-thioxo-1,3,4,5-tetrahydro-2H-pyrrolo[3,2-d]pyrimidin-2-one;
1-(2-isopropoxyethyl)-2-thioxo-1,2,3,5-tetrahydro-pyrrolo[3,2-d]pyrimidin-4-one;
1-(2-methoxy-2-methylpropyl)-2-thioxo-1,2,3,5-tetrahydro-pyrrolo[3,2-d]pyrimidin-4-one;
1-(2-ethoxy-2-methylpropyl)-2-thioxo-1,2,3,5-tetrahydro-pyrrolo[3,2-d]pyrimidin-4-one;
1-(piperidin-4-ylmethyl)-2-thioxo-1,2,3,5-tetrahydro-pyrrolo[3,2-d]pyrimidin-4-one;
1-[(1-methylpiperidin-3-yl)methyl]-2-thioxo-1,2,3,5-tetrahydro-pyrrolo[3,2-d]pyrimidin-4-one;
1-[2-hydroxy-2-(4-methoxyphenyl)ethyl]-2-thioxo-1,2,3,5-tetrahydro-pyrrolo[3,2-d]pyrimidin-4-one;
1-(2-methoxybenzyl)-2-thioxo-1,2,3,5-tetrahydro-pyrrolo[3,2-d]pyrimidin-4-one;
1-(3-methoxybenzyl)-2-thioxo-1,2,3,5-tetrahydro-pyrrolo[3,2-d]pyrimidin-4-one;
1-(2,4-dimethoxybenzyl)-2-thioxo-1,2,3,5-tetrahydro-pyrrolo[3,2-d]pyrimidin-4-one;
1-[(3-chloropyridin-2-yl)methyl]-2-thioxo-1,2,3,5-tetrahydro-pyrrolo[3,2-d]pyrimidin-4-one;
1-{[3-(2-ethoxyethoxy)pyridin-2-yl]methyl}-2-thioxo-1,2,3,5-tetrahydro-pyrrolo[3,2-d]pyrimidin-4-one;
1-[(6-oxo-1,6-dihydropyridin-2-yl)methyl]-2-thioxo-1,2,3,5-tetrahydro-pyrrolo[3,2-d]pyrimidin-4-one;
1-(1H-indol-3-ylmethyl)-2-thioxo-1,2,3,5-tetrahydro-pyrrolo[3,2-d]pyrimidin-4-one;
1-(1H-benzimidazol-2-ylmethyl)-2-thioxo-1,2,3,5-tetrahydro-pyrrolo[3,2-d]pyrimidin-4-one;
1-[(5-chloro-1H-indol-2-yl)methyl]-2-thioxo-1,2,3,5-tetrahydro-pyrrolo[3,2-d]pyrimidin-4-one;
1-[(5-fluoro-1H-indol-2-yl)methyl]-2-thioxo-1,2,3,5-tetrahydro-pyrrolo[3,2-d]pyrimidin-4-one;
1-(1H-indol-6-ylmethyl)-2-thioxo-1,2,3,5-tetrahydro-pyrrolo[3,2-d]pyrimidin-4-one;
1-(1H-indol-5-ylmethyl)-2-thioxo-1,2,3,5-tetrahydro-pyrrolo[3,2-d]pyrimidin-4-one;
1-[(5-fluoro-1H-indol-3-yl)methyl]-2-thioxo-1,2,3,5-tetrahydro-pyrrolo[3,2-d]pyrimidin-4-one;
1-(1H-imidazol-5-ylmethyl)-2-thioxo-1,2,3,5-tetrahydro-pyrrolo[3,2-d]pyrimidin-4-one;
1-(1H-imidazol-2-ylmethyl)-2-thioxo-1,2,3,5-tetrahydro-pyrrolo[3,2-d]pyrimidin-4-one;
1-[(5-chloro-1H-benzimidazol-2-yl)methyl]-2-thioxo-1,2,3,5-tetrahydro-pyrrolo[3,2-d]pyrimidin-4-one;
1-[(4,5-dimethyl-1H-benzimidazol-2-yl)methyl]-2-thioxo-1,2,3,5-tetrahydro-pyrrolo[3,2-d]pyrimidin-4-one;
7-bromo-1-isobutyl-2-thioxo-1,2,3,5-tetrahydro-pyrrolo[3,2-d]pyrimidin-4-one; and
1-(3-chlorophenyl)-2-thioxo-1,2,3,5-tetrahydro-pyrrolo[3,2-d]pyrimidin-4-one.

and pharmaceutically acceptable salts thereof.

A further aspect of the invention is the use of the novel compounds of formula (I) as a medicament.

A further aspect of the invention is the use of a compound of formula (I), or a pharmaceutically acceptable salt thereof, in the manufacture of a medicament, for the treatment or prophylaxis of diseases or conditions in which inhibition of the enzyme MPO is beneficial.

A further aspect of the invention provides the use of a compound of formula (I), or a pharmaceutically acceptable salt thereof, in the manufacture of a medicament, for the treatment or prophylaxis of neuroinflammatory disorders, cardio- and cerebrovascular atherosclerotic disorders and peripheral artery disease and respiratory disorders such as chronic obstructive pulmonary disease.

Another further aspect of the invention provides the use of a compound of formula (I), or a pharmaceutically acceptable salt thereof, in the manufacture of a medicament, for the treatment or prophylaxis of multiple sclerosis. Treatment may include slowing progression of disease.

Another further aspect of the present invention provides the use of a compound of formula (I) or a pharmaceutically acceptable salt thereof, in the manufacture of a medicament, for the treatment or prophylaxis of atherosclerosis by preventing and/or reducing the formation of new atherosclerotic lesions or plaques and/or by preventing or slowing progression of existing lesions and plaques.

Another further aspect of the present invention provides the use of a compound of formula (I) or a pharmaceutically acceptable salt thereof, in the manufacture of a medicament, for the treatment or prophylaxis of atherosclerosis by changing the composition of the plaques to reduce the risk of plaque rupture and atherothrombotic events.

Another further aspect of the present invention provides the use of a compound of formula (I) or a pharmaceutically acceptable salt thereof, in the manufacture of a medicament, for the treatment or prophylaxis of respiratory disorders, such as chronic obstructive pulmonary disease. Treatment may include slowing progression of disease.

According to the invention, there is also provided a method of treating, or reducing the risk of, diseases or conditions in which inhibition of the enzyme MPO is beneficial which comprises administering to a person suffering from or at risk of, said disease or condition, a therapeutically effective amount of a compound of formula (I), or a pharmaceutically acceptable salt thereof.

Further, there is also provided a method of treating, or reducing the risk of, neuroinflammatory disorders, cardio- and cerebrovascular atherosclerotic disorders or peripheral artery disease, or respiratory disorders, such as chronic obstructive pulmonary disease, in a person suffering from or at risk of, said disease or condition, wherein the method comprises administering to the person a therapeutically effective amount of a compound of formula (I), or a pharmaceutically acceptable salt thereof.

Further, there is also provided a method of treating, or reducing the risk of, multiple sclerosis in a person suffering from or at risk of, said disease or condition, wherein the method comprises administering to the person a therapeutically effective amount of a compound of formula (I), or a pharmaceutically acceptable salt thereof.

There is also provided a method of treating, or reducing the risk of atherosclerosis by preventing and/or reducing the formation of new atherosclerotic lesions or plaques and/or by preventing or slowing progression of existing lesions and plaques in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of atherosclerosis by changing the composition of the plaques so as to reduce the risk of plaque rupture and atherothrombotic events in a person suffering from or at risk of, said disease or condition, wherein the method comprises administering to the person a therapeutically effective amount of a compound of formula (I) or a pharmaceutically acceptable salt thereof.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of diseases or conditions in which inhibition of the enzyme MPO is beneficial.

In a further aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of neuroinflammatory disorders.

In a further aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of multiple sclerosis, cardio- and cerebrovascular atherosclerotic disorders and peripheral artery disease and respiratory disorders, such as chronic obstructive pulmonary disease.

In another aspect the present invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of atherosclerosis by preventing and reducing the formation of new atherosclerotic lesions and/or plaques and/or by preventing or slowing progression of existing lesions and plaques.

In another aspect the present invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of atherosclerosis by changing the composition of the plaques so as to reduce the risk of plaque rupture and atherothrombotic events.

According to the invention, there is further provided a process for the preparation of the novel compounds of formula (I), or a pharmaceutically acceptable salt, tautomer, enantiomer, diastereomer or racemate thereof which comprises reaction of a compound of formula (II),

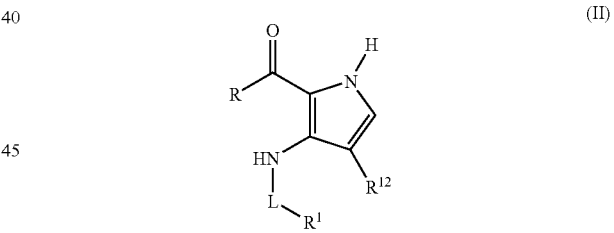

(II)

wherein $R^1$, $R^{12}$ and L are as defined in formula (I) and R represents C1 to 6 alkoxy with the oxygen in a direct bond to the carbonyl in formula (II) with alkoxy as defined above or $NH_2$;

with a C1 to 6 alkoxycarbonyl isothiocyanate or with a phenylcarbonyl isothiocyanate, wherein the phenyl group is optionally substituted by one or more groups selected independently from C1 to 6 alkyl, halogen, C1 to 6 alkoxy, $NO_2$, OH, CN, C1 to 6 alkylamino or $NH_2$; and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

In the process, a compound of formula (II) and the alkoxycarbonyl isothiocyanate or the phenylcarbonyl isothiocyanate are dissolved or suspended in a suitable dry organic solvent such as dichloromethane or and stirred at 0 to 30 degrees for example at ambient temperature until reaction is complete, typically for between 5 to 60 minutes, but if necessary, overnight. Preferably the alkoxycarbonyl isothiocyanate is ethoxycarbonyl isothiocyanate and the phenylcarbonyl isothiocyanate is preferably benzoyl isothiocyanate. Following a standard work-up the intermediate product is then optionally purified before treatment with a base, such as sodium ethoxide in ethanol, aqueous sodium hydroxide or ammonia in solution, ammonia in methanol, to give the required compound of formula (I). The cyclization is carried out at an elevated temperature either in an oil bath or in a microwave reactor. See, for example, Norman et al, *J. Med. Chem.* 2000, 43, 4288-4312. When ammonia in methanol is used, a pressure vessel is preferably used.

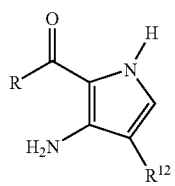
(III)

Compounds of formula (II) may be prepared by reaction of a compound of formula (III), wherein $R^{12}$ is as defined in Formula I, R is as defined in formula II (see for example Furneaux et al, *J. Org. Chem.* 1999, 64, 8411-8412), and may be carried out by

(IV)

a) reductive amination. In the process, a compound of formula (III) may be mixed with an aldehyde of formula (IV), wherein $R^1$ is defined as in formula I, in the presence of a reducing agent such as sodium cyanoborohydride or sodium triacetoxyborohydride. An acid, preferably acetic acid, may be added to catalyze the reaction. The reaction may be performed in a solvent such as methanol between ambient temperature and 50° C., preferably at ambient temperature. Following a standard work-up the product is then optionally purified by flash column chromatography. See for example Suzuki et al, *Chem. Pharm. Bull.* 2002, 50, 1163-1168, or Furneaux, R. H., Tyler, P. C., *J. Org. Chem.* 1999, 64, 8411-8412.

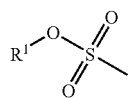
(V)

b) alkylation. In the process, a mesylate of formula (V), wherein $R^1$ is defined as above, may be added to a stirred solution of a compound of formula (III), potassium iodide and a base, preferably potassium carbonate. The reaction may be performed in a solvent, such as N,N-dimethylformamide, at an elevated reaction temperature, preferably at 85° C. The reaction mixture may be worked up by extraction and then purified by flash column chromatography to give a compound of formula (II).

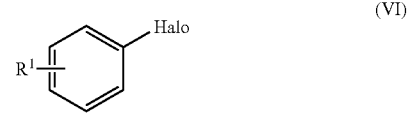
(VI)

c) cross-coupling of a compound of formula (II) with a suitable aryl of a compound (VI), wherein $R^1$ is defined as above and Halo is halogen, preferably bromo, to give a compound of formula (II). The reaction may be carried out using a suitable palladium catalyst such as $Pd_2(dba)_3$ or $Pd(OAc)_2$ together with a suitable ligand such as BINAP. A suitable base, such as cesium carbonate, may be used in the reaction in a suitable solvent such as tetrahydrofuran, dioxane or toluene, which is performed in the temperature range between 80° C. and 100° C. See for example, J. P. Wolfe, S. L. Buchwald *J. Org. Chem.* 2000, 65, 1144-1157.

Compounds of formula (II) are either known in the literature or may be prepared using known methods that will be readily apparent to the man skilled in the art. See, for example, Suzuki et al, *Chem. Pharm. Bull.* 2002, 50, 1163-1168, or Furneaux, R. H., Tyler, P. C., *J. Org. Chem.* 1999, 64, 8411-8412.

Compounds of formula (IV), (V) and (VI) are either commercially available or may be prepared using methods that are well-known in the literature.

The present invention includes compounds of formula (I) in the form of salts. Suitable salts include those formed with organic or inorganic acids or organic or inorganic bases. Such salts will normally be pharmaceutically acceptable although salts of non-pharmaceutically acceptable acids or bases may be of utility in the preparation and purification of the compound in question. Thus, preferred acid addition salts include those formed from hydrochloric, hydrobromic, sulphuric, phosphoric, citric, tartaric, lactic, pyruvic, acetic, is succinic, fumaric, maleic, methanesulphonic and benzenesulphonic acids. Preferred base addition salts include those in which the cation is sodium, potassium, calcium, aluminum, lithium, magnesium, zinc, choline, ethanolamine or diethylamine.

Salts of compounds of formula (I) may be formed by reacting the compound, or a salt, enantiomer or racemate thereof, with one or more equivalents of the appropriate acid or base. The reaction may be carried out in a solvent or medium in which the salt is insoluble or in a solvent in which the salt is soluble, for example, water, dioxan, ethanol, tetrahydrofuran or diethyl ether, or a mixture of solvents, which may be removed in vacuo or by freeze drying. The reaction may also be a metathetical process or it may be carried out on an ion exchange resin.

The compounds of the invention and intermediates thereto may be isolated from their reaction mixtures and, if necessary further purified, by using standard techniques.

The compounds of formula (I) may exist in enantiomeric forms. Therefore, all enantiomers, diastereomers, racemates, tautomers and mixtures thereof are included within the scope of the invention. The various optical isomers may be isolated by separation of a racemic mixture of the compounds using conventional techniques, for example, fractional crystallisation, or HPLC. Alternatively, the various optical isomers may be prepared directly using optically active starting materials.

Intermediate compounds may also exist in enantiomeric forms and may be used as purified enantiomers, diastereomers, racemates or mixtures.

The compounds of formula (I) may exist in tautomeric forms. All such tautomers and mixtures of tautomers are included within the scope of the invention.

Intermediate compounds may also exist in tautomeric forms and may be used as purified tautomers or mixtures.

The compounds of formula (I) and their pharmaceutically acceptable salts are useful because they possess pharmacological activity as inhibitors of the enzyme MPO.

The compounds of formula (I) and their pharmaceutically acceptable salts are indicated for use in the treatment or prophylaxis of diseases or conditions in which modulation of the activity of the enzyme myeloperoxidase (MPO) is desirable. In particular, linkage of MPO activity to disease has been implicated in neuroinflammatory diseases. Therefore the compounds of the present invention are particularly indicated for use in the treatment of neuroinflammatory conditions or disorders in mammals including man. The compounds are also indicated to be useful in the treatment of cardio- and cerebrovascular atherosclerotic disorders or peripheral artery disease. The compounds are also indicated to be useful in the treatment of respiratory disorders, such as disorders of the respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhintis including rhinitis nervosa (hay fever); nasal polyposis; acute viral infection including the common cold, and infection due to respiratory syncytial virus, influenza, coronavirus (including SARS) and adenovirus. Such conditions or disorders will be readily is apparent to the man skilled in the art.

Conditions or disorders that may be specifically mentioned include multiple sclerosis, Alzheimer's disease, Parkinson's disease, amyotrophic lateral sclerosis and stroke, as well as other inflammatory diseases or conditions such as asthma, chronic obstructive pulmonary disease, cystic fibrosis, idiopathic pulmonary fibrosis, acute respiratory distress syndrome, sinusitis, rhinitis, psoriasis, dermatitis, uveitis, gingivitis, atherosclerosis, myocardial infarction, stroke, coronary heart disease, ischaemic heart disease, restenosis, inflammatory bowel disease, renal glomerular damage, liver fibrosis, sepsis, proctitis, rheumatoid arthritis, and inflammation associated with reperfusion injury, spinal cord injury and tissue damage/scarring/adhesion/rejection. Lung cancer has also been suggested to be associated with high MPO levels. The compounds are also expected to be useful in the treatment of pain.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above-mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formulae (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another aspect of the invention concerns a pharmaceutical composition is comprising a novel compound of formula (I), or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formulae (I), or a pharmaceutically acceptable salt thereof.

There is also provided a process for the preparation of such a pharmaceutical composition which comprises mixing the ingredients.

EXAMPLES OF PHARMACEUTICAL COMPOSITION

The following illustrate representative pharmaceutical dosage forms containing a compound of formula I, or salts, solvates or solvated salts thereof, (hereafter compound X), for preventive or therapeutic use in mammals:

| (a): Tablet | mg/tablet |
|---|---|
| Compound X | 100 |
| Lactose | 182.75 |
| Croscarmellose sodium | 12.0 |
| Maize starch paste (5% w/v paste) | 2.25 |
| Magnesium stearate | 3.0 |

| (b): Capsule | mg/capsule |
|---|---|
| Compound X | 10 |
| Lactose | 488.5 |
| Magnesium stearate | 1.5 |

| (c): Injection | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | up to 100% |

The above compositions may be obtained by conventional procedures well known in the pharmaceutical art.

The invention further relates to combination therapies wherein a compound of formula (I) or a pharmaceutically acceptable salt thereof, or a pharmaceutical composition or formulation comprising a compound of formula (I), is administered concurrently or sequentially with therapy and/or an agent for the treatment of any one of cardio- and cerebrovascular atherosclerotic disorders and peripheral artery disease.

In particular, a compound of formula (I) or a pharmaceutically acceptable salt thereof may be administered in association with compounds from one or more of the following groups:

1) anti-inflammatory agents, for example
   a) NSAIDs (e.g. acetylsalicylic acid, ibuprofen, naproxen, flurbiprofen, diclofenac, indometacin);
   b) leukotriene synthesis inhibitors (5-LO inhibitors e.g. AZD4407, Zileuton, licofelone, CJ13610, CJ13454; FLAP inhibitors e.g. BAY-Y-1015, DG-031, MK591, MK886, A81834; LTA4 hydrolase inhibitors e.g. SC56938, SC57461A);
   c) leukotriene receptor antagonists (e.g. CP195543, amelubant, LY293111, accolate, MK571);

2) anti-hypertensive agents, for example
   a) beta-blockers (e.g. metoprolol, atenolol, sotalol);
   b) angiotensin converting enzyme inhibitors (e.g. captopril, ramipril, quinapril, enalapril);
   c) calcium channel blockers (e.g. verapamil, diltiazem, felodipine, amlodipine);
   d) angiotensin II receptor antagonists (e.g. irbesartan, candesartan, telemisartan, losartan);

3) anti-coagulantia, for example
   a) thrombin inhibitors (e.g. ximelagatran), heparines, factor Xa inhibitors;
   b) platelet aggregation inhibitors (e.g. clopidrogrel, ticlopidine, prasugel, AZ4160);

4) modulators of lipid metabolism, for example
   a) insulin sensitizers such as PPAR agonists (e.g. pioglitazone, rosiglitazone, Galida, muraglitazaar, gefemrozil, fenofibrate);
   b) HMG-CoA reductase inhibitors, statins (e.g. simvastatin, pravastatin, atorvaststin, rosuvastatin, fluvastatin);
   c) cholesterol absorption inhibitors (e.g. ezetimibe);
   d) IBAT inhibitors (e.g. AZD-7806);
   e) LXR agonists (e.g. GW-683965A, T-0901317);
   f) FXR receptor modulators;
   g) phospholipase inhibitors;

5) anti-anginal agents, for example, nitrates and nitrites;

6) modulators of oxidative stress, for example, anti-oxidants (probucol).

General Methods

All solvents used were analytical grade and commercially available anhydrous solvents were routinely used for reactions. Reactions were typically run under an inert atmosphere of nitrogen or argon.

$^1$H and $^{13}$C NMR spectra were recorded at 400 MHz for proton and 100 MHz for carbon-13 either on a Varian Unity+ 400 NMR Spectrometer equipped with a 5 mm BBO probe head with Z-gradients, or a Bruker Avance 400 NMR spectrometer equipped with a 60 µl dual inverse flow probe head with Z-gradients, or a Bruker DPX400 NMR spectrometer equipped with a 4-nucleus probe head equipped with Z-gradients. Unless specifically noted in the examples, spectra were recorded at 400 MHz for proton and 100 MHz for carbon-13. The following reference signals were used: the middle line of DMSO-$d_6$ δ 2.50 ($^1$H), δ 39.51 ($^{13}$C); the middle line of CD$_3$OD δ 3.31 ($^1$H) or δ 49.15 ($^{13}$C); acetone-$d_6$ 2.04 ($^1$H), 206.5 ($^{13}$C); and CDCl$_3$ δ 7.26 ($^1$H), the middle line of CDCl$_3$ δ 77.16 ($^{13}$C) (unless otherwise indicated).

Mass spectra were recorded on a Waters LCMS consisting of an Alliance 2795 (LC), Waters PDA 2996, and ELS detector (Sedex 75) and a ZMD single quadrupole mass spectrometer. The mass spectrometer was equipped with an electrospray ion source (ES) operated in a positive or negative ion mode. The capillary voltage was 3 kV and cone voltage was 30 V. The mass spectrometer was scanned between m/z 100-600 with a scan time of 0.7 s. The column temperature was set to 40° C. The Diode Array Detector was scanned from 200-400 nm. The temperature of the ELS detector was adjusted to 40° C. and the pressure was set to 1.9 bar. For LC separation a linear gradient was applied starting at 100% A (A: 10 mM NH$_4$OAc in 5% MeCN) and ending at 100% B (B: MeCN) after four minutes. The column used was a X-Terra MS C8, 3.0×50; 3.5 µM (Waters) run at 1.0 mL/min.

Alternatively, mass spectra was performed on a GC-MS (GC 6890, 5973N MSD) supplied by Agilent Technologies. The column used was a VF-5 MS, ID 0.25 mm×30 m, 0.25 µm (Varian Inc.). A linear temperature gradient was applied starting at 40° C. (hold 1 min) and ending at 300° C. (hold 1 min), 25° C./minute. The MS was equipped with a CI ion source and the reactant gas was methane. The MS was scanned between m/z 50-500 and the scan speed was set to 3.25 scan/s. The MS was equipped with an EI ion source. The MS was scanned between m/z 50-500 and the scan speed was set to 3.25 scan/s. The electron voltage was set to 70 eV.

HPLC analyses were performed on an Agilent HP1100 system consisting of G1379A Micro Vacuum Degasser, G1312A Binary Pump, G1367A Well plate auto-sampler, G1316A Thermostatted Column Compartment and G1315B Diode Array Detector. Column: X-Terra MS, Waters, 3.0× 100 mm, 3.5 µm. The column temperature was set to 40° C. and the flow-rate to 1.0 ml/min. The Diode Array Detector was scanned from 210-300 nm, step and peak width were set to 2 nm and 0.05 min, respectively. A linear gradient was applied, starting at 100% A (A: 10 mM NH$_4$OAc in 5% MeCN) and ending at 100% B (B: MeCN), in 6 min.

Microwave heating was performed in an Initiator or Smith Synthesizer Single-mode microwave cavity producing continuous irradiation at 2450 MHz.

A typical workup procedure after a reaction consisted of extraction of the product with a solvent such as ethyl acetate, washing with water followed by drying of the organic phase over MgSO$_4$ or Na$_2$SO$_4$ filtration and concentration of the solution in vacuo.

Thin layer chromatography (TLC) was performed on Merck TLC-plates (Silica gel 60 F$_{254}$) and UV visualized the spots. Flash column chromatography was preformed on a Combi Flash® Companion™ using RediSep™ normal-phase flash columns. Typical solvents used for flash column chromatography were mixtures of chloroform/methanol, dichloromethane/methanol and heptane/ethyl acetate.

Preparative chromatography was run on a Waters autopurification HPLC with a diode array detector. Column: XTerra MS C8, 19×300 mm, 10 µm. Narrow gradients with MeCN/ (95:5 0.1M NH$_4$OAc:MeCN) were used at a flow rate of 20 ml/min. Alternatively, another column was used; Atlantis C18 19×100 mm, 5 µm column. Gradient with acetonitrile/0.1M ammonium acetate in 5% acetonitrile in MilliQ Water, run from 0% to 35-50% acetonitrile, in 15 min. Flow rate: 15 ml/min. Alternatively, purification was achieved on a semi preparative Shimadzu LC-8A HPLC with a Shimadzu SPD-10A UV-vis-detector equipped with a Waters Symmetry® column (C18, 5 μm, 100 mm×19 mm). Narrow gradients with MeCN/0.1% trifluoroacetic acid in MilliQ Water were used at a flow rate of 10 ml/min.

Recrystallization was typically performed in solvents or solvent mixtures such as ether, ethyl acetate/heptane and methanol/water.

The following abbreviations have been used:

| | |
|---|---|
| aq. | aqueous; |
| BINAP | 2,2'bis(diphenylphosphino)-1,1'binaphtyl |
| equiv. | equivalent; |
| DMF | N,N-dimethylformamide; |
| DMSO | dimethylsulfoxide; |
| DIBAL | diisobutylaluminium hydride; |
| Et$_3$N | triethyl amine; |
| HOAc | acetic acid; |
| NaBH$_4$ | sodium borohydride; |
| NaCNBH$_3$ | sodium cyanoborohydride; |
| Pd$_2$(dba)$_3$ | tris(dibenaylideneacetone)dipalladium; |
| Pd(OAc)$_2$ | palladium diacetate; |
| r.t. | room temperature; |
| TBDMSCl | tert-butyldimethylsilyl chloride; |
| TEMPO | 2,2,6,6-tetramethyl-1-piperidinyloxy |
| THF | tetrahydrofuran. |

Starting materials used were either available from commercial sources or prepared according to literature procedures and had experimental data in accordance with those reported. The following is an example of a starting material that was prepared: 3-Amino-1H-pyrrole-2-carboxylic acid ester: Furneaux, R. H., Tyler, P. C., *J. Org. Chem.* 1999, 64, 8411-8412.

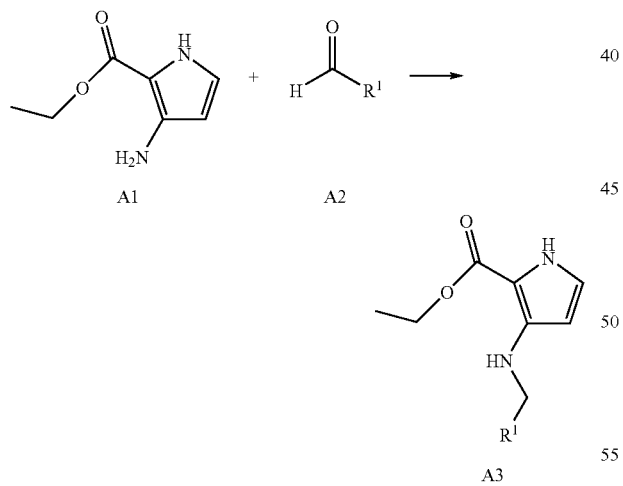

General Method A

A reaction mixture of the amino pyrrole ester A1 (1.0 equiv.), the aldehyde A2 (1.0 to 2.0 equiv.) and NaCNBH$_3$ (1.0 equiv.) in methanol was stirred at r.t. for 24 h. In some examples, acetic acid (1 to 2 equiv.) was added to catalyze the reaction. If the reaction was not complete after 24 h (monitored by TLC or LC-MS), more aldehyde A2 was added and the mixture was stirred at r.t. until the reaction was complete. The mixture was then evaporated onto silica gel and purified by flash column chromatography.

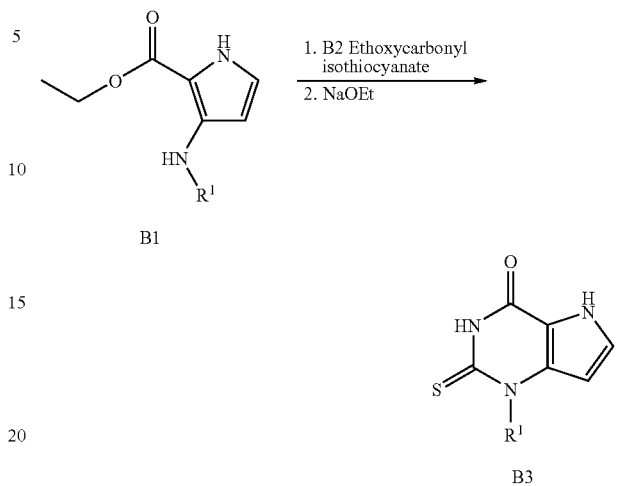

General Method B

Ethoxycarbonyl isothiocyanate B2 (1.0 to 1.2 equiv.) was added to the amino pyrrole ester B1 (1.0 equiv.) in CH$_2$Cl$_2$ and the mixture was stirred at r.t. for 5 to 60 minutes, or overnight. Water was added and the aqueous phase was extracted with CH$_2$Cl$_2$. The organic phase was combined, dried (MgSO$_4$) and concentrated. The crude ring opened intermediate was purified by flash column chromatography. The intermediate product was dissolved in 1M NaOEt in EtOH (1.1-1.5 equiv.) and heated in a microwave reactor for 10 minutes at 120° C. The pH was adjusted to neutral pH with 2M HCl; the solid was collected by filtration and washed with water. The crude product was purified using preparative HPLC, or by flash column chromatography or by recrystallization.

The invention is illustrated, but in no way limited, by the following examples. Except where otherwise indicated, the compounds of Examples 1a to 4a and 5c and 7b were prepared using the procedure of General Method A, and the compounds of Examples 1b to 4b and 5d and 7c were prepared using the procedure of General Method B.

Example 1

1-Butyl-2-thioxo-1,2,3,5-tetrahydro-pyrrolo[3,2-d]pyrimidin-4-one (a) 3-(Butylamino)-1H-pyrrole-2-carboxylic acid ethyl ester The title compound was obtained as an oil in 60% yield starting from 3-amino-1H-pyrrole-2-carboxylic acid ethyl ester (0.81 g, 5.26 mmol) and butyraldehyde (0.47+0.55 mL, 11.4 mmol).

$^1$H NMR (DMSO-d$_6$) δ ppm 10.71 (1H, br s), 6.74 (1H, t, J=3.1 Hz), 5.62 (1H, t, J=2.6 Hz) 5.19 (1H, s), 4.17 (2H, q, J=7.0 Hz), 3.04 (2H, q, J=6.6 Hz), 1.50 (2H, m), 1.34 (2H, m), 1.25 (3H, t, J=7.0 Hz), 0.90 (3H, t, J=7.3 Hz);

MS (ESI) m/z 211 (M+1).

(b) 1-Butyl-2-thioxo-1,2,3,5-tetrahydro-pyrrolo[3,2-d]pyrimidin-4-one

The title compound was obtained as a solid in 44% yield starting from 3-(butylamino)-1H-pyrrole-2-carboxylic acid ethyl ester (0.10 g, 0.48 mmol) and ethoxycarbonyl isothiocyanate (0.06 mL, 0.58 mmol).

$^1$H NMR (DMSO-d$_6$) δ ppm 12.38 (1H, s), 12.10 (1H, s), 7.37 (1H, d, J=2.9), 6.31 (1H, d, J=2.6 Hz), 4.36 (2H, m), 1.69 (2H, m), 1.38 (2H, m), 0.92 (3H, t, J=7.5 Hz);

MS (ESI) m/z 224 (M+1).

Example 2

1-Isobutyl-2-thioxo-1,2,3,5-tetrahydro-pyrrolo[3,2-d]pyrimidin-4-one (a) 3-(Isobutylamino)-1H-pyrrole-2-carboxylic acid ethyl ester The title compound was obtained as an oil in 71% yield starting from 3-amino-1H-pyrrole-2-carboxylic acid ethyl ester (0.40 g, 2.59 mmol) and isobutyraldehyde (0.26+0.07 mL, 3.61 mmol).

$^1$H NMR (DMSO-d$_6$) δ ppm 10.68 (1H, s), 6.74 (1H, t, J=3.0 Hz), 5.62 (1H, t, J=2.4 Hz), 5.30 (1H, br s), 4.18 (2H, q, J=7.2 Hz), 2.88 (2H, t, J=6.4 Hz), 1.79 (1H, m), 1.26 (3H, t, J=7.1 Hz), 0.90 (3H, s), 0.89 (3H, s);

$^{13}$C NMR (DMSO-d$_6$) δ ppm 160.9, 124.2, 95.0, 58.2, 52.4, 27.9, 20.0, 14.7;

MS (ESI) m/z 211 (M+1).

(b) 1-Isobutyl-2-thioxo-1,2,3,5-tetrahydro-pyrrolo[3,2-d]pyrimidin-4-one

The title compound was obtained as a solid in 24% yield starting from 3-(isobutylamino)-1H-pyrrole-2-carboxylic acid ethyl ester (0.38 g, 1.79 mmol) and ethoxycarbonyl isothiocyanate (0.24 mL, 2.15 mmol).

$^1$H NMR (DMSO-d$_6$) δ ppm 12.36 (1H, br s), 12.13 (1H, br s), 7.35 (1H, d, J=2.8 Hz), 6.34 (1H, d, J=2.8 Hz), 4.21 (2H, d, =7.33 Hz), 2.44 (1H, m), 0.91 (3H, s), 0.90 (3H, s);

$^{13}$C NMR (DMSO-d$_6$) δ ppm 172.8, 152.4, 137.3, 127.7, 113.6, 97.1, 56.2, 26.4, 19.7;

MS (ESI) m/z 224 (M+1).

Example 3

1-(Pyridin-2-ylmethyl)-2-thioxo-1,2,3,5-tetrahydro-pyrrolo[3,2-d]pyrimidin-4-one (a) 3-[(Pyridin-2-ylmethyl)amino]-1H-pyrrole-2-carboxylic acid ethyl ester The title compound was obtained as an oil in 54% yield starting from 3-amino-1H-pyrrole-2-carboxylic acid ethyl ester (0.40 g, 2.59 mmol) and 2-pyridinecarboxaldehyde (0.27+0.07 mL, 3.55 mmol).

$^1$H NMR (DMSO-d$_6$) δ ppm 10.77 (1H, br s), 8.52 (1H, d, J=4.0 Hz), 7.80-7.67 (1H, m), 7.35 (1H, d, J=7.8 Hz), 7.25 (1H, dd, J=7.3, 5.0 Hz), 6.71 (1H, t, J=3.0 Hz), 6.10 (1H, br s), 5.57 (1H, t, J=2.4 Hz), 4.37 (2H, d, J=5.8 Hz), 4.21 (2H, q, J=7.2 Hz), 1.29 (3H, t, J=7.1 Hz);

MS (ESI) m/z 246 (M+1).

(b) 1-(Pyridin-2-ylmethyl)-2-thioxo-1,2,3,5-tetrahydro-pyrrolo[3,2-d]pyrimidin-4-one The title compound was obtained as a solid in 14% yield starting from 3-[(pyridin-2-ylmethyl)amino]-1H-pyrrole-2-carboxylic acid ethyl ester (0.34 g, 1.39 mmol) and ethoxycarbonyl isothiocyanate (0.19 mL, 1.66 mmol).

$^1$H NMR (DMSO-d$_6$) δ ppm 12.34 (2H, br s), 8.49 (1H, d, J=4.5 Hz), 7.73 (1H, m), 7.29 (1H, d, J=2.8 Hz), 7.27 (1H, m), 7.21 (1H, d, J=7.8 Hz), 6.09 (1H, d, J=2.8 Hz), 5.75 (2H, s);

$^{13}$C NMR (DMSO-d$_6$) δ ppm 173.4, 155.2, 152.6, 149.1, 137.1, 136.8, 127.9, 122.4, 121.2, 113.6, 96.9, 54.2;

MS (ESI) m/z 259 (M+1).

Example 4

1-(2-Fluoro-benzyl)-2-thioxo-1,2,3,5-tetrahydro-pyrrolo[3,2-d]pyrimidin-4-one (a) 3-(2-Fluoro-benzylamino)-1H-pyrrole-2-carboxylic acid ethyl ester The title compound was obtained as an oil in quantitative yield starting from 3-amino-1H-pyrrole-2-carboxylic acid ethyl ester (0.50 g, 3.2 mmol), and 2-fluorobenzaldehyde (0.34 mL, 3.2 mmol) using the general procedure A but with the following modifications. After 5 h more NaCNBH$_3$ (100 mg, 1.6 mmol) was added followed by more 2-fluorobenzaldehyde (120 mg, 1 mmol), and the reaction was then stirred overnight.

$^1$H NMR (DMSO-d$_6$) δ ppm 10.76 (1H, br s), 7.47 (1H, m), 7.38 (1H, m), 7.28 (2H, m), 6.70 (1H, m), 5.74 (1H, br s), 5.61 (1H, m), 4.34 (2H, m), 4.18 (2H, q, J=7.1 Hz), 1.25 (3H, t, J=7.1 Hz);

MS (ES) m/z 263 (M+1).

(b) 1-(2-Fluoro-benzyl)-2-thioxo-1,2,3,5-tetrahydro-pyrrolo[3,2-d]pyrimidin-4-one The title compound was obtained as a solid in 45% yield starting from 3-(2-fluoro-benzylamino)-1H-pyrrole-2-carboxylic acid ethyl ester (0.85 g, 3.2 mmol) and ethoxycarbonyl isothiocyanate (0.44 mL, 3.9 mmol).

$^1$H NMR (DMSO-d$_6$) δ ppm 12.41 (2H, br s.), 7.33 (2H, m), 7.24 (1H, m), 7.10 (1H, m, J=7.5, 7.5 Hz), 7.01 (1H, m, J=7.1 Hz, 7.1 Hz), 6.12 (1H, d, J=2.8 Hz), 5.72 (2H, s);

$^{13}$C NMR (DMSO-d$_6$) δ 173.9, 161.4, 159.0, 152.9, 137.1, 129.6, 129.5, 128.5, 128.1, 128.1, 125.0, 124.9, 123.2, 123.0, 115.8, 115.6, 114.1, 96.9, 47.1, 47.1;

MS (ESI) m/z 276 (M+1).

Example 5

1-[2-(2-Methoxyethoxy)-3-propoxybenzyl]-2-thioxo-1,2,3,5-tetrahydro-pyrrolo[3,2-d]pyrimidin-4-one (a) 3-Hydroxy-2-(2-methoxyethoxy)benzaldehyde 2-Chloroethyl methyl ether (4.63 mL, 50.7 mmol) was added dropwise to a mixture of 2,3-dihydroxybenzaldehyde (7.0 g, 50.7 mmol), potassium iodide (8.41 g, 50.69 mmol) and potassium carbonate (7.71 g, 55.8 mmol) in DMF (80 mL). The resulting mixture was stirred at r.t. under a nitrogen atmosphere for two days and at 70° C. for two days. The reaction mixture was partitioned between saturated ammonium chloride (aq.) and CH$_2$Cl$_2$. The water phase was re-extracted with CH$_2$Cl$_2$ and the combined organic phases were washed with brine, dried (Na$_2$SO$_4$) and evaporated onto silica. Purification by flash column chromatography (heptane/ethyl acetate gradient; 0 to 30% ethyl acetate) yielded a crude oil which was further purified by flash column chromatography (heptane/ethyl acetate gradient; 0 to 40% ethyl acetate) to yield the title compound (3.13 g, 31%) as an oil.

¹H NMR (DMSO-d₆) δ ppm 10.34 (1H, br s), 9.88 (1H, br s), 7.16 (2H, m), 7.05 (1H, m), 4.25 (2H, m), 3.60 (2H, m), 3.26 (3H, m);
¹³C NMR (DMSO-d₆) δ ppm 190.5, 150.7, 149.6, 129.9, 124.1, 122.6, 116.9, 72.1, 70.9, 57.9;
MS (ESI) m/z 197 (M+1).

(b) 2-(2-Methoxyethoxy)-3-propoxybenzaldehyde

1-Iodopropane (3.09 mL, 31.60 mmol) was added to a solution of 3-hydroxy-2-(2-methoxyethoxy)benzaldehyde (3.1 g, 15.8 mmol) and potassium carbonate (4.37 g, 31.60 mmol) in DMF (80 mL) and the mixture was stirred at 100° C. overnight under a nitrogen atmosphere. The reaction mixture was partitioned between saturated ammonium chloride (aq.) and $CH_2Cl_2$. The organic phase was washed with brine, dried ($Na_2SO_4$) and concentrated to give the title compound in quantitative yield (3.8 g) as an oil. This material was used in the next step without further purification.
¹H NMR (DMSO-d₆) δ ppm 10.37 (1H, s), 7.36 (1H, m, J=8.0 Hz), 7.26 (1H, m), 7.17 (1H, t, J=7.8 Hz), 4.28 (2H, m), 4.02 (2H, t, J=6.3 Hz), 3.62 (2H, m), 3.26 (3H, s), 1.80 (2H, m), 1.02 (3H, t, J=7.3 Hz);
¹³C NMR (DMSO-d₆) δ ppm 190.3, 152.1, 150.9, 129.6, 124.4, 119.4, 117.8, 72.5, 70.9, 70.0, 57.9, 22.1, 10.4;
MS (ESI) m/z 239 (M+1).

(c) 3-{[2-(2-Methoxyethoxy)-3-propoxybenzyl] amino}-1H-pyrrole-2-carboxylic acid ethyl ester The title compound was obtained as an oil in quantitative yield starting from 3-amino-1H-pyrrole-2-carboxylic acid ethyl ester (0.35 g, 2.27 mmol) and 2-(2-methoxyethoxy)-3-propoxybenzaldehyde (0.47+0.08 g, 3.06 mmol).
¹H NMR (DMSO-d₆) δ ppm 10.69 (1H, br s), 7.13 (1H, s), 7.6.99 (2H, m), 6.70 (1H, m), 5.63 (1H, m), 4.92 (1H, t, J=5.7 Hz), 4.52 (2H, d, J=5.8 Hz), 4.19 (2H, m), 4.05 (2H, m), 3.92 (2H, t, J=6.4 Hz), 3.59 (2H, m), 3.32 (3H, s), 1.76 (2H, m), 1.26 (3H, t, J=7.1 Hz), 1.00 (3H, m);
MS (ESI) m/z 377 (M+1).

(d) 1-[2-(2-Methoxyethoxy)-3-propoxybenzyl]-2-thioxo-1,2,3,5-tetrahydro-pyrrolo[3,2-d]pyrimidin-4-one The title compound was obtained as a solid in 13% yield starting from 3-{[2-(2-methoxyethoxy)-3-propoxybenzyl] amino}-1H-pyrrole-2-carboxylic acid ethyl ester (0.87 g, 2.31 mmol) and ethoxycarbonyl isothiocyanate (0.26 mL, 2.31 mmol).
¹H NMR (DMSO-d₆) δ ppm 12.43 (1H, br s), 12.31 (1H, br s), 7.29 (1H, d, J=3.0 Hz), 6.96-6.85 (2H, m), 6.41 (1H, dd, J=7.3, 1.5 Hz), 6.02 (1H, d, J=2.8 Hz), 5.71 (2H, s), 4.23 (2H, m), 3.95 (2H, t, J=6.3 Hz), 3.65 (2H, m), 3.33 (3H, s), 1.82-1.72 (2H, m), 1.02 (3H, t, J=7.4 Hz);
MS (ESI) m/z 390 (M+1).

Example 6

1-(6-Ethoxy-pyridin-2-ylmethyl)-2-thioxo-1,2,3,5-tetrahydro-pyrrolo[3,2-d]pyrimidin-4-one (a) 6-Ethoxy-pyridine-2-carboxylic acid ethyl ester Ethyl iodide (2.3 mL, 28.8 mmol) was added to a suspension of 6-hydroxy-pyridine-2-carboxylic acid (1.0 g, 7.2 mmol) and silver(I) carbonate (4.0 g, 14.4 mmol) in $CHCl_3$ (70 mL). The suspension was stirred at ambient temperature for 3 days. Insoluble material was removed by filtration and the solid was washed with $CHCl_3$. The filtrate was concentrated to give the title product in quantitative yield (1.5 g) as an oil. This material was used in the next step without further purification.
¹H NMR (CDCl₃) δ ppm 7.65 (2H, m), 6.88 (1H, m), 4.45 (2H, q, J=7.0 Hz), 4.41 (2H, q, J=7.3 Hz), 1.40 (6H, m);
MS (ESI) m/z 196 (M+1).

(b) (6-Ethoxy-pyridin-2-yl)-methanol $NaBH_4$ (5.7 g, 151 mmol) was added in portions during 35 minutes to 6-ethoxy-pyridine-2-carboxylic acid ethyl ester (1.5 g, 7.5 mmol) in EtOH (75 mL). The resulting mixture was stirred at ambient temperature for two days. Water was added and the mixture was extracted with $CH_2Cl_2$. The organic phase was dried ($Na_2SO_4$), filtered and then concentrated to give the title product (0.85 g) in 74% yield as an oil. This material was used in the next step without further purification.
¹H NMR (CDCl₃) δ ppm 7.55 (1H, m), 6.77 (1H, d, J=7.4 Hz), 6.61 (1H, d, J=8.1 Hz), 4.66 (2H, d, J=5.3 Hz), 4.38 (2H, q, J=7.1 Hz), 3.46 (1H, t, J=5.2 Hz), 1.41 (3H, t, J=7.1 Hz).

(c) 6-Ethoxy-pyridine-2-carbaldehyde

DMSO (0.50 mL, 6.4 mmol) in $CH_2Cl_2$ (10 mL) was added dropwise to a solution of oxalyl chloride (2M in $CH_2Cl_2$, 3.1 mL, 6.1 mmol) in $CH_2Cl_2$ (20 mL) at −60° C. The resulting mixture was stirred at −60° C. for 10 minutes. (6-Ethoxy-pyridin-2-yl)-methanol (0.85 g, 5.6 mmol) in $CH_2Cl_2$ (5 mL) and DMSO (4 mL) was added dropwise. The mixture was stirred at −60° C. for 3 h, and was then allowed to warm to −20° C. and $Et_3N$ (6 mL) was added. The resulting solution was stirred at ambient temperature for 40 minutes. Water was added and the mixture was extracted with $CH_2Cl_2$. The organic phase was washed with brine, dried ($Na_2SO_4$), and concentrated. Diethyl ether was added to the residue and insoluble material was removed by filtration. The filtrate was concentrated to yield the title compound (0.60 g) in 70% yield as a solid. This crude product was used in the next step without further purification.
¹H NMR (CDCl₃) δ ppm 9.93 (1H, s), 7.71 (1H, m), 7.53 (1H, d, J=7.1 Hz), 6.94 (1H, d, J=8.3 Hz), 4.46 (2H, d, J=7.1 Hz), 1.42 (3H, t, J=7.1 Hz).

(d) 3-[(6-Ethoxy-pyridin-2-ylmethyl)-amino]-1H-pyrrole-2-carboxylic acid ethyl ester Acetic acid (0.3 mL) was added to 6-ethoxy-pyridine-2-carbaldehyde (0.59 g, 3.9 mmol) and 3-amino-1H-pyrrole-2-carboxylic acid ethyl ester (0.30 g, 1.9 mmol) in ethanol (10 mL). After 1.5 h, $NaCNBH_3$ (0.24 g, 3.9 mmol) was added, and the resulting mixture was stirred at ambient temperature for 19 h. The solvent was removed in vacuo, ethyl acetate was added to the residue, and insoluble material was removed by filtration. The filtrate was concentrated and the crude product was purified by flash column chromatography (heptane/ethyl acetate gradient; 0 to 35% ethyl acetate), obtaining 0.25 g (45%) of the title product as a solid.
¹H NMR (CDCl₃) δ ppm 8.16 (1H, br s), 7.50 (1H, m), 6.89 (1H, d, J=7.3 Hz), 6.70 (1H, br s), 6.57 (1H, d, J=8.1 Hz), 4.45 (2H, q, J=7.0 Hz), 5.71 (1H, m), 4.38 (5H, m), 1.37 (6H, m);
MS (ESI) m/z 290 (M+1).

(e) 1-(6-Ethoxy-pyridin-2-ylmethyl)-2-thioxo-1,2,3, 5-tetrahydro-pyrrolo[3,2-d]pyrimidin-4-one Ethoxycarbonyl isothiocyanate (0.12 g, 0.90 mmol) was added to 3-[(6-ethoxy-pyridin-2-ylmethyl)-amino]-1H-pyrrole-2-carboxylic acid ethyl ester (0.24 g, 0.82 mmol) in $CH_2Cl_2$ (5 mL) and the solution was stirred at ambient temperature for 35 minutes. The solvent was evaporated and 0.4M NaOEt in ethanol (3 mL, 1.2 mmol) was added to the residue and the mixture was refluxed for 1 h. More NaOEt (0.4M in ethanol, 1.5 mL, 0.6 mmol) was added and the solution was refluxed for another 1.5 h. The solvent was evaporated, the residue was dissolved in water and the pH adjusted to neutral pH with 1M HCl. The resulting solid was collected, washed, and dried to give crude product. This material was purified by preparative HPLC to yield the title compound (38 mg, 15%) as a solid.

$^1$H NMR (DMSO-$d_6$) δ ppm 12.32 (2H, br s), 7.62 (1H, m), 7.29 (1H, d, J=3.0 Hz), 6.78 (1H, d, J=7.3 Hz), 6.64 (1H, d, J=8.3 Hz), 6.13 (1H, d, J=2.8 Hz), 5.65 (2H, s), 4.17 (2H, q, J=7.1 Hz), 1.19 (3H, 7, J=7.0 Hz);

$^{13}$C NMR (DMSO-$d_6$) δ 173.5, 162.7, 152.8, 152.5, 139.6, 137.2, 127.8, 113.9, 113.6, 109.0, 97.0, 61.0, 53.8, 14.3;

MS (ESI) m/z 303 (M+1).

Example 7

1-Piperidin-3-ylmethyl-2-thioxo-1,2,3,5-tetrahydro-pyrrolo[3,2-d]pyrimidin-4-one

(a) 3-Formyl-piperidine-1-carboxylic acid tert-butyl ester

DMSO (0.18 mL, 2.6 mmol) in $CH_2Cl_2$ (5 mL) was added dropwise to a solution of oxalyl chloride (2M in $CH_2Cl_2$, 0.65 mL, 1.3 mmol) in $CH_2Cl_2$ (4 mL) at −78° C. The resulting mixture was stirred at −68° C. for 15 minutes. 3-Hydroxymethyl-piperidine-1-carboxylic acid tert-butyl ester (Dean A. Wacker et al. *Bioorganic & Medicinal Chemistry Letters* 2002, 12, 1785-1789) (0.22 g, 1.0 mmol) in $CH_2Cl_2$ (4 mL) was added dropwise and after 15 min stirring at −78° C., $Et_3N$ (6 mL) was added. The resulting solution was stirred at ambient temperature for 16 h. Water was added and the mixture was extracted with diethyl ether, the organic layer was dried ($Na_2SO_4$) and concentrated to give the product as an yellow oil (0.20 g, 92% yield). This crude product was used in the next step without further purification.

MS (ESI) m/z 214 (M+1).

(b) 3-[(2-Ethoxycarbonyl-1H-pyrrol-3-ylamino)-methyl]-piperidine-1-carboxylic acid tert-butyl ester The title compound was obtained as an oil in 30% yield starting from 3-amino-1H-pyrrole-2-carboxylic acid ethyl ester (0.14 g, 0.92 mmol) and 3-formyl-piperidine-1-carboxylic acid tert-butyl ester (0.20 g, 0.92 mmol).

$^1$H NMR (CDCl$_3$) δ ppm 8.29 (1H, br s), 6.70 (1H, s), 5.67 (1H, m), 4.27 (2H, m), 3.93 (1H, br s), 3.85 (1H, d, J=13.2 Hz), 3.10-2.94 (2H, m), 2.83 (1H, m), 2.65 (1H, br s), 1.85 (1H, m), 1.76 (1H, m), 1.64 (1H, m), 1.42 (9H, s), 1.31 (3H, t, J=6.8 Hz), 1.22 (1H, m);

MS (ESI) m/z 352 (M+1).

(c) 1-Piperidin-3-ylmethyl-2-thioxo-1,2,3,5-tetrahydro-pyrrolo[3,2-d]pyrimidin-4-one The title compound was obtained as a solid in 20% yield using 3-[(2-ethoxycarbonyl-1H-pyrrol-3-ylamino)-methyl]-piperidine-1-carboxylic acid tert-butyl ester (97 mg, 0.27 mmol) and ethoxycarbonyl isothiocyanate (36 mg, 0.27 mmol) using the general procedure B, with the following modifications. After the base mediated cyclization reaction, 6M HCl (0.3 mL) was added to the reaction followed by heating in a microwave reactor for 4 minutes at 100° C. The solvent was removed in vacuo and the residual solid was purified by preparative HPLC using Atlantis C18 19×100 mm, 5 μm column. Gradient with acetonitrile/0.1M ammonium acetate in 5% acetonitrile in MilliQ Water, run from 0% to 50% acetonitrile, in 15 min. Flow rate: 15 ml/min.

$^1$H NMR (Methanol-$d_4$) δ ppm 7.23 (1H, d, J=3.2 Hz), 6.21 (1H, d, J=3.2 Hz), 4.46 (1H, m), 4.23 (1H, m), 3.22 (2H, m), 2.86 (2H, m), 2.58 (1H, m), 1.83 (2H, m), 1.62 (1H, m), 1.42 (1H, m);

$^{13}$C NMR (Methanol-$d_4$) δ 178.8, 154.7, 139.3, 129.5, 115.3, 97.8, 53.7, 48.0, 45.2, 34.5, 27.6, 23.2;

MS (ESI) m/z 265 (M+1).

Example 8

1-Butyl-4-thioxo-1,3,4,5-tetrahydro-2H-pyrrolo[3,2-d]pyrimidin-2-one

Ethoxycarbonyl isothiocyanate (0.13 ml, 1.1 mmol) was added to 3-(butylamino)-1H-pyrrole-2-carboxylic acid ethyl ester (0.23 g, 1.1 mmol) in toluene (5 mL) and the mixture was heated at 90° C. for 1 h. The precipitate was filtered off and washed with hexane. The intermediate product was treated with potassium hydroxide (0.55 g, 9.9 mmol) in water (9 mL), and heated to reflux for 15 h. After cooling to ambient temperature, the pH was adjusted to pH 5 with 12 M HCl. The resultant precipitate was collected by filtration and washed with water. The crude product was purified using preparative HPLC to give the title compound (16 mg, 6%) as a solid.

$^1$H NMR (DMSO-$d_6$) δ ppm 12.04 (1H, br s), 11.95 (1H, br s), 7.40 (1H, s), 6.23 (1H, d, J=2.7 Hz), 3.84 (2H, t, J=7.2 Hz), 1.66-1.56 (2H, m), 1.32 (2H, m), 0.89 (3H, t, J=7.3 Hz);

MS (ESI) m/z 224 (M+1).

Example 9

1-(2-Isopropoxyethyl)-2-thioxo-1,2,3,5-tetrahydro-pyrrolo[3,2-d]pyrimidin-4-one

(a) 3-[(2-Isopropoxyethyl)amino]-1H-pyrrole-2-carboxylic acid ethyl ester

Trichlorocyanuric acid (1.84 g, 7.93 mmol) was added to a solution of 2-isopropoxyethanol (0.75 g, 7.21 mmol) in $CH_2Cl_2$ (3 mL). The reaction mixture was cooled to 0° C. and TEMPO (0.022 g, 0.14 mmol) was carefully added in small portions. The mixture was stirred at r.t. for 20 minutes then filtered through Celite and washed with $CH_2Cl_2$. The filtrate was kept cold, 0° C., during filtration. The aldehyde solution was added to a stirred mixture of 3-amino-1H-pyrrole-2-carboxylic acid ester (0.83 g, 5.41 mmol) and HOAc (0.62 mL, 10.8 mmol) at 0° C. in methanol (5 mL). The mixture was stirred for 20 minutes, then NaCNBH$_3$ (0.34 g, 5.41 mmol) was added. After stirring at r.t for 2 h, the solution was evaporated onto silica and purified by flash column chromatography (heptane/ethyl acetate gradient; 0 to 100% ethyl acetate) to yield the title compound (0.75 g, 58%) as an oil.
$^1$H NMR (DMSO-d$_6$) δ ppm 10.72 (1H, br s), 6.76-6.74 (1H, m), 5.66-5.65 (1H, m), 5.34 (1H, br s), 4.17 (2H, q, J=7.0 Hz), 3.59-3.49 (3H, m), 3.15 (2H, q, J=5.6 Hz), 1.26 (3H, t, J=7.0 Hz), 1.10 (3H, s), 1.08 (3H, s);
MS (ESI) m/z 241 (M+1).

(b) 1-(2-Isopropoxyethyl)-2-thioxo-1,2,3,5-tetrahydro-pyrrolo[3,2-d]pyrimidin-4-one The title compound (0.17 g, 23%) was prepared in accordance with the general method B using 3-[(2-isopropoxyethyl)amino]-1H-pyrrole-2-carboxylic acid ethyl ester (0.7 g, 2.91 mmol) and ethoxycarbonyl isothiocyanate (0.40 mL, 3.50 mmol).
$^1$H NMR (DMSO-d$_6$) δ ppm 12.74 (2H, br s), 7.35 (1H, d, J=2.8 Hz), 6.29 (1H, d, J=3.0 Hz), 4.49 (2H, t, J=6.3 Hz), 3.72 (2H, t, J=6.3 Hz), 3.60-3.58 (1H, m), 1.02 (3H, s), 1.01 (3H, s);
MS (ESI) m/z 254 (M+1).

Example 10

1-(2-Methoxy-2-methylpropyl)-2-thioxo-1,2,3,5-tetrahydro-pyrrolo[3,2-d]pyrimidin-4-one (a) 3-[(2-Methoxy-2-methylpropyl)amino]-1H-pyrrole-2-carboxylic acid ester The title compound was obtained as an oil in 75% yield starting from 3-amino-1H-pyrrole-2-carboxylic acid ethyl ester (0.250 g, 1.62 mmol) and 2-methoxy-2-methylpropanal (U.S. Pat. No. 3,652,579) (0.331 g, 3.24 mmol) using the general procedure A but with the following modifications. After 6 h more 2-methoxy-2-methylpropanal (0.165 g, 1,62 mmol) was added, and the reaction mixture was then stirred overnight.
$^1$H NMR (DMSO-d$_6$) δ ppm 10.69 (1H, br s), 6.74 (1H, t, J=3.0 Hz), 5.64 (1H, t, J=2.6 Hz), 5.33 (1H, br s), 4.17 (2H, q, J=7.1 Hz), 3.11 (3H, s), 3.03 (2H, d, J=5.8 Hz), 1.26 (3H, t, J=7:1 Hz,), 1.13 (6H, s);
MS (ESI) m/z 241 (M+1).

(b) 1-(2-Methoxy-2-methylpropyl)-2-thioxo-1,2,3,5-tetrahydro-pyrrolo[3,2-d]pyrimidin-4-one The title compound was obtained as a solid in 3% yield starting from 3-[(2-ethoxy-2-methylpropyl)amino]-1H-pyrrole-2-carboxylic acid ethyl ester (0.283 g, 1.18 mmol) and ethoxycarbonyl isothiocyanate (0.13 mL, 1.18 mmol) using the general procedure B but with the following modification. The reaction was run in a microwave reactor for a total of 35 minutes.
$^1$H NMR (DMSO-d$_6$) δ ppm 12.29 (1H, br s), 12.17 (1H, br s), 7.30 (1H, d, J=2.76), 6.29 (1H, d, J=2.76), 4.58 (2H, br s), 3.12 (3H, s), 1.21 (6H, s);
MS (ESI) m/z 254 (M+1).

Example 11

1-(2-Ethoxy-2-methylpropyl)-2-thioxo-1,2,3,5-tetrahydro-pyrrolo[3,2-d]pyrimidin-4-one (a) 2-Bromo-1,1-diethoxy-2-methylpropane The product was synthesized according to a modified procedure described in U.S. Pat. No. 3,652,579. Bromine water (2.95 mL, 57.6 mmol) was added dropwise to isobutyraldehyde (4.82 g, 66.8 mmol) in ethanol (22 mL) and the resulting mixture was stirred at r.t. for 40 minutes. More bromine water (0.3 mL, 5.86 mmol) was added. The reaction mixture was neutralized by addition of calcium carbonate (3.5 g, 25.3 mmol). The remaining calcium carbonate was filtered off and the filtrate was poured onto an ice-water mixture. The aqueous phase was extracted with CH$_2$Cl$_2$, dried (Na$_2$SO$_4$), filtered and concentrated. After vacuum distillation, the title product (10.10 g, 67%) was obtained.
$^1$H NMR (DMSO-d$_6$) δ ppm 4.43 (1H, s), 3.80-3.73 (2H, m), 1.64 (6H, s), 1.15 (6H, t, J=7.1 Hz).

(b) 2-Ethoxy-2-methylpropanal

The product was synthesized according to a procedure described in U.S. Pat. No. 3,652,579. 2-Ethoxy-2-methylpropanal (5.63 g, 25 mmol) was added dropwise to potassium bitartrate (2.35 g, 12.5 mmol) in refluxing deionized water (22.5 mL) over 50 minutes. The resulting mixture was refluxed for 70 minutes. The solvent and product were distilled off. Ammonium sulfate (total 8.5 g) was added to the product-solvent mixture. The mixture was stirred and then the two phases were separated and the upper phase was distilled from calcium chloride obtaining the title product (1.60 g, 55%).
MS (CI) m/z 117 (M+1).

(c) 3-[(2-Ethoxy-2-methylpropyl)amino]-1H-pyrrole-2-carboxylic acid ethyl ester

The title compound was obtained as an oil in 63% yield starting from 3-amino-1H-pyrrole-2-carboxylic acid ethyl ester (0.200 g, 1.30 mmol) and 2-ethoxy-2-methyl propionaldehyde (0.292 g, 2.86 mmol) using the general procedure A but with the following modification. The reaction mixture was stirred at r.t. for 48 h.
$^1$H NMR (CDCl$_3$) δ ppm 6.74 (1H, br s), 5.70 (1H, br s), 4.32 (2H, q, J=7.4 Hz), 3.54-3.47 (2H, m), 3.44 (2H, q, J=7.6 Hz), 3.12 (2H, d, J=4 Hz), 1.25 (6H, s), 1.20 (3H, t, J=7.4 Hz), 1.19 (3H, t, J=7.6 Hz);
MS (ESI) m/z 255 (M+1).

(d) 1-(2-Ethoxy-2-methylpropyl)-2-thioxo-1,2,3,5-tetrahydro-pyrrolo[3,2-d]pyrimidin-4-one 3-(2-Methoxy-2-methyl)-propylamino-1H-pyrrole-2 carboxylic acid ethyl ester (0.200 g, 0.79 mmol) was dissolved in CH$_2$Cl$_2$ (2 mL) at r.t. under a nitrogen atmosphere. Ethoxycarbonyl isothiocyanate (0.12 mL, 1.02 mmol) was added dropwise and the reaction mixture was stirred at r.t. overnight. The solvent was evaporated and sodium ethoxide (1M in ethanol, 0.94 mL, 0.94 mmol) was added and the reaction was heated to 40° C. for 48 h. Water (2 mL) was added and the pH was adjusted to neutral pH with 2M HCl. The precipitate was collected by filtration and was purified by preparative HPLC to give the title compound in 6% yield (0.12 g).
$^1$H NMR (DMSO-d$_6$) δ ppm 12.22 (1H, br s), 7.30 (1H, d, J=2.8 Hz), 6.35 (1H, d, J=3 Hz), 4.60 (2H, br s), 3.40-3.34 (3H, m), 1.22 (6H, s), 1.04 (3H, t, J=7.0 Hz);
MS (ESI) m/z 267 (M+1).

Example 12

1-(Piperidin-4-ylmethyl)-2-thioxo-1,2,3,5-tetrahydro-pyrrolo[3,2-d]pyrimidin-4-one (a) 4-[(2-(Ethoxycarbonyl)-1H-pyrrol-3-ylamino)-methyl]piperidine-4-carboxylic acid tert-butyl ester The title compound (0.156 g, 10%) was prepared in accordance with general method A starting from 3-amino-1H-pyrrole-2-carboxylic acid ethyl ester (0.68 g, 4.4 mmol) and 4-formylpiperidine-1-carboxylic acid tert-butyl ester (P. C. Ting et al., *Bioorganic & Medicinal Chemistry Letters,* 2001, 11, 491-494) (0.98 g, 4.6 mmol.

$^1$H NMR (DMSO-$d_6$) δ ppm 10.70 (1H, br s), 6.74 (1H, br s), 5.65 (1H, br s), 4.19 (2H, q, J=7.2 Hz), 3.95 (2H, d, J=12.0 Hz), 2.97 (2H, t, J=6.0 Hz), 2.65 (2H, br s), 1.66 (2H, d, J=12.0 Hz), 1.39 (9H, s), 1.26 (3H, t, J=7.2 Hz), 1.07-0.95 (2H, m);

MS (ESI) m/z 352 (M+1).

(b) 1-(Piperidin-4-ylmethyl)-2-thioxo-1,2,3,5-tetrahydro-pyrrolo[3,2-d]pyrimidin-4-one Ethoxycarbonyl isothiocyanate (0.058 g, 0.44 mmol) was added to a stirred solution of 4-[(2-(ethoxycarbonyl)-1H-pyrrol-3-ylamino)-methyl]piperidine-1-carboxylic acid tert-butyl ester (0.156 g, 0.44 mmol) in $CH_2Cl_2$ (2 mL) and the mixture was stirred at r.t. for 1 h. The solvent was removed in vacuo and the residue was taken up in ethanol (1 mL) containing sodium (0.015 g, 0.66 mmol). The resulting mixture was heated in a microwave reactor at 120° C. for 10 minutes. 6M HCl (0.5 mL) was added and the reaction mixture was heated again in the microwave at 100° C. for 3 minutes. The pH was adjusted to neutral pH with 2M HCl and the solution was concentrated in vacuo. The crude product was purified by preparative HPLC to give the title compound (0.038 g, 14%) as a white solid.

$^1$H NMR (DMSO-$d_6$) δ ppm 7.36 (1H, d, J=2.8 Hz), 6.33 (1H, d, J=2.8 Hz), 4.27 (2H, br s), 2.95 (2H, d, J=12.0 Hz), 2.40 (2H, t, J=10.4 Hz), 2.25-2.15 (1H, m), 1.50 (2H, d, J=10.8 Hz), 1.37-1.20 (2H, m);

$^{13}$C NMR (DMSO-$d_6$) δ ppm 173.2, 152.9, 137.6, 128.1, 114.0, 97.5, 55.2, 45.5, 34.7, 30.0;

MS (ESI) m/z 265 (M+1).

Example 13

1-[(1-Methylpiperidin-3-yl)methyl]-2-thioxo-1,2,3,5-tetrahydro-pyrrolo[3,2-d]pyrimidin-4-one 1-Piperidin-3-ylmethyl-2-thioxo-1,2,3,5-tetrahydro-pyrrolo[3,2-d]pyrimidin-4-one (Example 7) (0.092 g, 0.35 mmol) was dissolved in methanol (2 mL) and formic acid (37% aq., 0.059 mL, 0.7 mmol) was added. After 5 minutes of stirring at r.t. a precipitate had formed. $NaCNBH_3$ (0.026 g, 0.42 mmol) was added and the mixture was stirred at r.t. for 1 h. The solvent was removed in vacuo and the residual solid was purified by preparative HPLC, obtaining the title compound (0.022 g, 22%) as a white solid.

$^1$H NMR (DMSO-$d_6$) δ ppm 12.22 (1H, br s), 7.36 (1H, d, J=2.8 Hz), 6.33 (1H, s), 4.27 (2H, br s), 2.61-2.5 (1H, m), 2.36-2.30 (1H, m), 2.09 (3H, s), 1.93-1.82 (3H, m), 1.65-1.52 (2H, m), 1.44-1.32 (1H, m), 1.16-1.07 (1H, m);

$^{13}$C NMR (DMSO-$d_6$) δ ppm 173.2, 152.9, 137.6, 128.1, 114.0, 97.3, 59.2, 56.0, 53.3, 46.7, 34.9, 27.7, 24.7;

MS (ESI) m/z 279 (M+1).

Example 14

1-[2-Hydroxy-2-(4-methoxyphenyl)ethyl]-2-thioxo-1,2,3,5-tetrahydro-pyrrolo[3,2-d]pyrimidin-4-one (a) Methyl {[tert-butyl(dimethyl)silyl]oxy}(4-methoxyphenyl)acetate TBDMSCl (1.5 g, 9.94 mmol) and imidazole (1.0 g, 14.6 mmol) were added to a solution of methyl hydroxy-(4-methoxyphenyl)acetate (Teodozyj Kolasa et al., *J. Org. Chem.,* 1987, 22, 4978-4984) (1.3 g, 6.62 mmol) in DMF (8 mL) and the mixture was stirred at r.t. for 2 h. Water was added and the mixture was extracted with diethyl ether. The organic layer was washed with brine, dried ($MgSO_4$), filtered and concentrated to give the title compound (2.0 g, 97%).

$^1$H NMR ($CDCl_3$) δ ppm 7.39 (2H, d, J=8.8 Hz), 6.88 (2H, d, J=8.8 Hz), 5.19 (1H, s), 3.81 (3H, s), 3.69 (3H, s), 0.92 (9H, s), 0.11 (3H, s), 0.03 (3H, s).

(b) {[tert-Butyl(dimethyl)silyl]oxy}(4-methoxyphenyl)acetaldehyde

Methyl {[tert-butyl(dimethyl)silyl]oxy}(4-methoxyphenyl)acetate (0.5 g, 1.61 mmol) was dissolved in toluene (10 mL) and cooled to −78° C. under a nitrogen atmosphere. DIBAL (1.0M in toluene, 1.9 mL, 1.93 mmol) was added slowly and the mixture was stirred at −78° C. for 1 h. The reaction mixture was poured onto a mixture of ice (20 g) and $CHCl_3$ (20 mL). The mixture was stirred at r.t. for 30 minutes. The layers were separated and the water phase extracted with $CHCl_3$. The organic phase was washed with brine, dried ($MgSO_4$), filtered and concentrated, obtaining 99% (0.45 g) of the title compound. The product was used directly in the next step without further purification.

$^1$H NMR ($CDCl_3$) δ ppm 7.40-7.38 (2H, m), 6.89-6.87 (2H, m), 5.19 (1H, s), 3.81 (3H, s), 0.92 (9H, s), 0.11 (3H, s), 0.03 (3H, s).

(c) 3-{[2-{[tert-Butyl(dimethyl)silyl]oxy}-2-(4-methoxyphenyl)ethyl]amino}-1H-pyrrole-2-carboxylic acid ethyl ester The title compound (0.13 g, 19%) was prepared in accordance with general method A using 3-amino-1H-pyrrole-2-carboxylic acid ethyl ester (0.16 g, 1.07 mmol) and {[tert-butyl(dimethyl)silyl]oxy}(4-methoxyphenyl)acetaldehyde (0.3 g, 1.07 mmol).

MS (ESI) m/z 417 (M−1).

(d) 1-[2-{[tert-Butyl(dimethyl)silyl]oxy}-2-(4-methoxyphenyl)ethyl]-2-thioxo-1,2,3,5-tetrahydro-pyrrolo[3,2-d]pyrimidin-4-one The title compound (0.07 g, 90%) was prepared in accordance with general method B using 3-{[2-{[tert-butyl(dimethyl)silyl]oxy}-2-(4-methoxyphenyl)ethyl]amino}-1H-pyrrole-2-carboxylic acid ethyl ester (0.13 g, 0.31 mmol) and ethoxycarbonyl isothiocyanate (0.042 mL, 0.37 mmol).

$^1$H NMR (DMSO-$d_6$) δ ppm 12.28-12.23 (2H, m), 7.42 (2H, d, J=8.6 Hz), 7.34-7.33 (1H, m), 6.96 (2H, d, J=8.6 Hz), 6.33 (1H, br s), 5.53-5.50 (1H, m), 4.57 (1H, br s), 4.15 (1H, br s), 3.76 (3H, s), 0.61 (9H, s), 0.31 (3H, s), 0.39 (3H, s);

MS (ESI) m/z 432 (M+1).

(e) 1-[2-Hydroxy-2-(4-methoxyphenyl)ethyl]-2-thioxo-1,2,3,5-tetrahydro-pyrrolo[3,2-d]pyrimidin-4-one Tetra-n-butylammonium fluoride (1M in THF, 1.27 mL, 1.27 mmol) was added to 1-[2-{[tert-butyl(dimethyl)silyl]oxy}-2-(4-methoxyphenyl)ethyl]-2-thioxo-1,2,3,5-tetrahydro-pyrrolo[3,2-d]pyrimidin-4-one (0.065 g, 0.152 mmol) in THF (8 mL). The mixture was stirred at 50° C. overnight. Ethyl acetate was added, and the organic phase was washed with water and brine, dried ($MgSO_4$), filtered and concentrated. This crude material was purified by preparative HPLC to yield the title compound (0.018 g, 37%) as a solid.

$^1$H NMR (DMSO-$d_6$) δ ppm 12.20 (2H, br s), 7.40 (2H, d, J=8.5 Hz), 7.29 (1H, d, J=2.8 Hz), 6.91 (2H, d, J=8.8 Hz), 6.27 (1H, d, J=2.8 Hz), 5.42-5.41 (1H, m), 5.28-5.24 (1H, m), 4.62-4.58 (1H, m), 4.19-4.16 (1H, m), 3.74 (3H, s);

MS (ESI) m/z 316 (M−1).

Example 15

1-(2-Methoxybenzyl)-2-thioxo-1,2,3,5-tetrahydro-pyrrolo[3,2-d]pyrimidin-4-one

(a) 3-[(2-Methoxybenzyl)amino]-1H-pyrrole-2-carboxylic acid ethyl ester

The title compound was obtained as a white solid in quantitative yield starting from 3-amino-1H-pyrrole-2-carboxylic acid ethyl ester (0.350 g, 2.27 mmol) and ortho-anisaldehyde (0.37 g, 2.71 mmol) using general procedure A but with the following modifications. After stirring overnight, the reaction mixture was evaporated. The crude solid was taken up in $CHCl_3$, filtered and the solvent was evaporated in vacuo, and this crude product was used in the next step without further purification.

MS (ESI) m/z 275 (M+1).

(b) 1-(2-Methoxybenzyl)-2-thioxo-1,2,3,5-tetrahydro-pyrrolo[3,2-d]pyrimidin-4-one The title compound was obtained as a solid in 16% yield starting from 3-[(2-methoxybenzyl)amino]-1H-pyrrole-2-carboxylic acid ethyl ester (0.622 g, 2.27 mmol) and ethoxycarbonyl isothiocyanate (0.26 mL, 2.27 mmol) using general procedure B but with the following modification. The intermediate crude product was dissolved in 1M NaOEt (2.27 mL, 2.27 mmol) and was stirred at 80° C. for 3 h.

$^1$H NMR (DMSO-$d_6$) δ ppm 12.36 (2H, br s), 7.27 (1H, d, J=2.8 Hz), 7.27-7.21 (1H, m), 7.06 (1H, d, J=8.1 Hz), 6.82 (1H, t, J=7.3 Hz), 6.79-6.75 (1H, m), 5.96 (1H, d, J=2.8 Hz), 5.61 (2H, s), 3.89 (3H, s);

MS (ESI) m/z 288 (M+1).

Example 16

1-(3-Methoxybenzyl)-2-thioxo-1,2,3,5-tetrahydro-pyrrolo[3,2-d]pyrimidin-4-one

(a) 3-[(3-Methoxybenzyl)amino]-1H-pyrrole-2-carboxylic acid ethyl ester

The title compound was obtained as an oil in 57% (0.508 g) yield and was prepared in accordance with general method A using 3-amino-1H-pyrrole-2-carboxylic acid ethyl ester (0.50 g, 3.24 mmol) and m-anisaldehyde (0.47 mL, 3.89 mmol).

$^1$H NMR (DMSO-$d_6$) δ ppm 10.73 (1H, br s), 7.24-7.20 (1H, m), 6.90-6.86 (1H, m), 6.80-6.77 (1H, m), 6.71-6.69 (1H, m), 5.75 (1H, br s), 5.59-5.58 (1H, m), 4.46 (1H, d, J=5.8 Hz), 4.25 (2H, d, J=6.3 Hz), 4.19 (2H, q, J=7.1 Hz), 3.72 (3H, s), 1.26 (3H, t, J=7.1 Hz);

MS (ESI) m/z 275 (M+1).

(b) 1-(3-Methoxybenzyl)-2-thioxo-1,2,3,5-tetrahydro-pyrrolo[3,2-d]pyrimidin-4-one The title compound was obtained as a solid in 3% (0.014 g) yield and was prepared in accordance with general method B using 3-[(3-methoxybenzyl)amino]-1H-pyrrole-2-carboxylic acid ethyl ester (0.494 g, 1.80 mmol) and ethoxycarbonyl isothiocyanate (0.20 mL, 1.18 mmol).

$^1$H NMR (DMSO-$d_6$) δ ppm 12.41-12.34 (2H, m), 7.29 (1H, d, J=2.7 Hz), 7.23 (1H, t, J=8.0 Hz), 6.93-6.91 (1H, m), 6.86 (1H, d, J=7.8 Hz), 6.83 (1H, dd, J=8.2, 2.4 Hz), 6.14 (1H, d, J=2.8 Hz), 5.67 (2H, s), 3.71 (3H, s);

MS (ESI) m/z 288 (M+1).

Example 17

1-(2,4-Dimethoxybenzyl)-2-thioxo-1,2,3,5-tetrahydro-pyrrolo[3,2-d]pyrimidin-4-one

(a) 3-[(2,4-Dimethoxybenzyl)amino]-1H-pyrrole-2-carboxylic acid ethyl ester The title compound was obtained as an oil in 85% (0.838 g) yield and was prepared in accordance with general method A using 3-amino-1H-pyrrole-2-carboxylic acid ethyl ester (0.50 g, 3.24 mmol) and 2,4-dimethoxybenzaldehyde (0.647 g, 3.89 mmol).

$^1$H NMR (DMSO-$d_6$) δ ppm 10.69 (1H, br s), 7.14 (1H, d, J=8.3 Hz), 6.71 (1H, t, J=3.0 Hz), 6.54 (1H, d, J=2.3 Hz), 6.44 (1H, dd, J=8.3 Hz), 5.66 (1H, t, J=2.5 Hz), 5.59 (1H, br s), 4.20-4.13 (4H, m), 3.80 (3H, s), 3.73 (3H, s), 1.25 (3H, t, J=7.1 Hz);

$^{13}$C NMR (DMSO-$d_6$) δ ppm 160.9, 159.6, 158.0, 129.2, 124.0, 120.0, 104.2, 98.3, 95.5, 58.3, 55.4, 55.1, 43.6, 14.7;

MS (ESI) m/z 303 (M−1).

(b) 1-(2,4-Dimethoxybenzyl)-2-thioxo-1,2,3,5-tetrahydro-pyrrolo[3,2-d]pyrimidin-4-one The title compound was obtained as a solid in 14% (0.118 g) yield and was prepared in accordance with general method B using 3-[(2,4-dimethoxybenzyl)amino]-1H-pyrrole-2-carboxylic acid ethyl ester (0.828 g, 2.72 mmol) and ethoxycarbonyl isothiocyanate (0.31 mL, 2.72 mmol).

$^1$H NMR (DMSO-$d_6$) δ ppm 12.41 (1H, br s), 12.27 (1H, s), 7.27 (1H, t, J=2.9 Hz), 6.77 (1H, d, J=8.3 Hz), 6.61 (1H, d, J=2.3 Hz), 6.41 (1H, dd, J=8.5, 2.4 Hz), 5.95 (1H, t, J=2.3 Hz), 5.54 (2H, s), 3.88 (3H, s), 3.72 (3H, s);

MS (ESI) m/z 318 (M+1).

Example 18

1-[(3-Chloropyridin-2-yl)methyl]-2-thioxo-1,2,3,5-tetrahydro-pyrrolo[3,2-d]pyrimidin-4-one

(a) 3-{[(3-chloropyridin-2-yl)methyl]amino}-1H-pyrrole-2-carboxylic acid ethyl ester The title compound was obtained as a solid in 91% (0.225 g) yield and was prepared in accordance with general method A using 3-amino-1H-pyrrole-2-carboxylic acid ethyl ester (0.231 g, 1.50 mmol) and 3-chloropyridine-2-carbaldehyde (Nadeem Iqbal et al., *J. Med. Chem.* 1998, 41, 1827-1837) (0.212 g, 1.50 mmol).

$^1$H NMR (DMSO-d$_6$) δ ppm 10.81 (1H, br s), 8.53-8.51 (1H, m), 7.94-7.92 (1H, m), 7.40-7.36 (1H, m), 6.77-6.76 (1H, m), 5.74-5.73 (1H, m), 4.43 (1H, d, J=5.5 Hz), 4.20-4.15 (2H, m), 1.30-1.27 (3H, m);

MS (ESI) m/z 280 (M+1).

(b) 1-[(3-Chloropyridin-2-yl)methyl]-2-thioxo-1,2,3,5-tetrahydro-pyrrolo[3,2-d]pyrimidin-4-one The title compound was obtained as a solid in 5% (0.011 g) yield and was prepared in accordance with general method B using 3-{[(3-chloropyridin-2-yl)methyl]amino}-1H-pyrrole-2-carboxylic acid ethyl ester (0.215 g, 0.77 mmol) and ethoxycarbonyl isothiocyanate (0.09 mL, 0.77 mmol).

$^1$H NMR (DMSO-d$_6$) δ ppm 12.26 (1H, br s), 8.32-8.30 (1H, m), 7.96-7.93 (1H, m), 7.34-7.30 (1H, m), 7.28 (1H, d, J=3.0 Hz), 6.16 (1H, d, J=2.8 Hz), 5.80 (2H, s);

MS (ESI) m/z 293 (M+1).

Example 19

1-{[3-(2-Ethoxyethoxy)pyridin-2-yl]methyl}-2-thioxo-1,2,3,5-tetrahydro-pyrrolo[3,2-d]pyrimidin-4-one

(a) 3-(2-Ethoxyethoxy)-2-methylpyridine

Potassium carbonate (2.20 g, 15.9 mmol) was added to a stirred solution of 3-hydroxy-2-methylpyridine (1.45 g, 13.3 mmol) and 2-chloroethyl ethyl ether (1.75 mL, 15.9 mmol) in DMF (7 mL) and the mixture was stirred at 70° C. overnight. The reaction was not complete and additional 2-chloroethyl ethyl ether (1 equiv.) and potassium carbonate (1 equiv.) were added and the mixture was stirred at 85° C. for 8 h. Water and ethyl acetate were added and the aqueous layer was extracted with ethyl acetate. The organic layer was dried (MgSO$_4$), filtered and concentrated. The crude product was purified by flash column chromatography (heptane/ethyl acetate gradient; 0 to 50% ethyl acetate), obtaining 1.80 g (75%) the title compound.

$^1$H NMR (DMSO-d$_6$) δ ppm 8.03-7.99 (1H, m), 7.33-7.31 (1H, m), 7.18-7.14 (1H, m), 4.13-4.11 (2H, m), 3.73-3.71 (2H, m), 3.52 (2H, q, J=7.0 Hz), 2.35 (3H, s), 1.12 (3H, t, J=6.9 Hz);

MS (ESI) m/z 182 (M+1).

(b) 3-(2-Ethoxyethoxy)pyridine-2-carbaldehyde

A mixture of 3-(2-ethoxyethoxy)-2-methylpyridine (0.506 g, 2.79 mmol) and selenium dioxide (0.31 g, 2.79 mmol) in 1,4-dioxane (10 mL) was heated at 75° C. overnight. After cooling to r.t., the mixture was filtered and the solids were washed with ethyl acetate. The solvent was removed in vacuo. The reaction was not complete and the solid was dissolved in 1,4 dioxane (15 mL) and selenium dioxide (0.31 g, 2.79 mmol) was added. The mixture was heated at 110° C. overnight. Ethyl acetate (10 mL) was added and the mixture was filtered. The black solid was washed with ethyl acetate and the filtrate was evaporated in vacuo. The crude product was purified by flash column chromatography (heptane/ethyl acetate gradient; 0 to 100% ethyl acetate), obtaining 0.21 g (39%) of the title compound.

$^1$H NMR (DMSO-d$_6$) δ ppm 10.23 (1H, s), 8.35 (1H, d, J=4.3 Hz), 7.77 (1H, d, J=8.6 Hz), 7.66-7.62 (1H, m), 4.29 (2H, m), 3.75 (2H, m), 3.55-3.49 (2H, m), 1.14-1.09 (3H, m).

(c) 3-({[3-(2-Ethoxyethoxy)pyridin-2-yl]methyl}amino)-1H-pyrrole-2-carboxylic acid ethyl ester The title compound (0.17 g, 73%) was prepared in accordance with general method A using 3-(2-ethoxyethoxy)pyridine-2-carbaldehyde (0.21 g, 1.08 mmol) and 3-amino-1H-pyrrole-2-carboxylic acid ethyl ester (0.11 g, 0.717 mmol).

$^1$H NMR (DMSO-d$_6$) δ ppm 10.76 (1H, s), 8.13-8.12 (1H, m), 7.46-7.44 (1H, m), 7.30-7.28 (1H, m), 6.76-6.75 (1H, m), 6.29 (1H, br s), 5.71-5.70 (1H, m), 4.32-4.31 (2H, m), 4.22-4.17 (4H, m), 3.77-3.74 (2H, m), 3.57-3.51 (2H, m), 1.30 (3H, t, J=7.0 Hz), 1.15-1.12 (3H, m);

MS (ESI) m/z 334 (M+1).

(d) 1-{[3-(2-Ethoxyethoxy)pyridin-2-yl]methyl}-2-thioxo-1,2,3,5-tetrahydro-pyrrolo[3,2-d]pyrimidin-4-one The title compound (0.051 g, 28%) was prepared in accordance with general method B using 3-({[3-(2-ethoxyethoxy)pyridin-2-yl]methyl}amino)-1H-pyrrole-2-carboxylic acid ethyl ester (0.17 g, 0.52 mmol) and ethoxycarbonyl isothiocyanate (0.07 mL, 0.62 mmol).

$^1$H NMR (DMSO-d$_6$) δ ppm 12.32-12.19 (2H, m), 7.92 (1H, d, J=4.0 Hz), 7.47 (1H, d, J=7.8 Hz), 7.32-7.14 (2H, m), 5.98 (1H, d, J=2.8 Hz), 5.73 (2H, s), 4.26-4.23 (2H, m), 3.78-3.76 (2H, m), 3.55 (2H, q, J=7.1 Hz), 1.14 (3H, t, J=6.9 Hz);

$^{13}$C NMR (DMSO-d$_6$) δ 173.5, 152.7, 152.4, 143.7, 140.3, 137.8, 127.7, 123.0, 119.0, 113.5, 96.8, 68.2, 65.8, 49.8, 15.1;

MS (ESI) m/z 347 (M+1).

Example 20

1-[(6-Oxo-1,6-dihydropyridin-2-yl)methyl]-2-thioxo-1,2,3,5-tetrahydro-pyrrolo[3,2-d]pyrimidin-4-one

(a) 3-{[(6-Oxo-1,6-dihydropyridin-2-yl)methyl]amino}-1H-pyrrole-2-carboxylic acid ethyl ester 6-Oxo-1,6-dihydropyridine-2-carbaldehyde (WO 2002/006272) (0.31 g, 2.5 mmol) was dissolved in EtOH (10 mL). 3-Amino-1H-pyrrole-2-carboxylic acid ethyl ester (0.19 g, 1.3 mmol) was added, followed by HOAc (0.14 mL, 2.5 mmol). The mixture was stirred for 75 minutes at r.t. and then NaCNBH$_3$ (0.16 g, 2.5 mmol) was added. The reaction mixture was stirred at r.t. overnight. The solvent was evaporated in vacuo and the crude product was purified by flash column chromatography (CH$_2$Cl$_2$/methanol gradient; 0 to 10% methanol), obtaining 0.288 g (85%) of the title product as an oil that crystallized upon standing.

¹H NMR (DMSO-d₆) δ ppm 11.57 (1H, br s), 10.77 (1H, br s), 7.34-7.30 (1H, m), 6.71-6.70 (1H, m), 6.16-6.13 (2H, m), 5.98 (1H, br s), 5.75 (1H, s), 5.64-5.63 (1H, m), 4.20 (2H, q, J=7.1 Hz), 4.09-4.08 (2H, m), 1.27 (3H, t, J=7.1 Hz);
MS (ESI) m/z 262 (M+1).

(b) 1-[(6-Oxo-1,6-dihydropyridin-2-yl)methyl]-2-thioxo-1,2,3,5-tetrahydro-pyrrolo[3,2-d]pyrimidin-4-one Benzoyl isothiocyanate (0.27 g, 1.6 mmol) dissolved in CH₂Cl₂ (3 mL) was added to 3-{[(6-oxo-1,6-dihydropyridin-2-yl)methyl]amino}-1H-pyrrole-2-carboxylic acid ethyl ester (0.25 g, 0.96 mmol) in CH₂Cl₂ (7 mL). The resulting mixture was stirred at r.t. overnight. The solvent was removed in vacuo and the residue was dissolved in methanol (15 mL) and potassium carbonate (0.50 g, 3.6 mmol) was added. The reaction mixture was stirred at 50° C. for 6.5 h. After cooling to r.t., 1M HCl was added dropwise until a neutral pH was obtained. The resulting precipitate was collected, washed with methanol and purified by preparative HPLC to obtain the title compound (0.097 g, 37%) as a solid.
¹H NMR (DMSO-d₆) δ ppm 12.46-12.38 (2H, m), 11.69 (1H, br s), 7.34-7.29 (2H, m), 6.23 (2H, s), 5.75 (1H, br s), 5.49 (2H, s);
¹³C NMR (DMSO-d₆) δ 173.6, 162.7, 152.5, 140.6, 136.7, 128.0, 113.6, 96.6;
MS (ESI) m/z 275 (M+1).

Example 21

1-(1H-Indol-3-ylmethyl)-2-thioxo-1,2,3,5-tetrahydro-pyrrolo[3,2-d]pyrimidin-4-one (a) Ethyl 3-[(1H-indol-3-ylmethyl)amino]-1H-pyrrole-2-carboxylate A reaction mixture of 3-amino-1H-pyrrole-2-carboxylic acid ethyl ester (0.075 g, 0.49 mmol), indole-3-carboxaldehyde (0.085 g, 0.58 mmol), NaCNBH₃ (0.031 g, 0.49 mmol) and HOAc (0.056 mL, 0.97 mmol) in methanol (3 mL) was stirred at r.t. overnight. The mixture was concentrated in vacuo and the crude product-mixture was used in the next step without further purification.
MS (ESI) m/z 284 (M+1).

(b) 1-(1H-Indol-3-ylmethyl)-2-thioxo-1,2,3,5-tetrahydro-pyrrolo[3,2-d]pyrimidin-4-one A crude mixture of ethyl 3-[(1H-indol-3-ylmethyl)amino]-1H-pyrrole-2-carboxylate (max 0.49 mmol) was added to CH₂Cl₂ (5 mL). A few drops of methanol were added to increase solubility. Benzoylisothiocyanate (0.072 g, 0.53 mmol) was added and the mixture was stirred at r.t. for 1 h. The mixture was concentrated in vacuo. Ammonia (7N in methanol, 3 mL) was added and the mixture was heated at 80° C. for 2 h. The mixture was concentrated and purified by preparative HPLC, obtaining the title compound (0.030 g, 21%) as a solid.
¹H NMR (DMSO-d₆) δ ppm 12.13 (2H, br s), 11.08 (1H, s), 7.87 (1H, d, J=8.1 Hz), 7.54-747 (1H, m), 7.38-7.30 (1H, m), 7.29-7.25 (1H, m), 7.10-7.03 (1H, m), 7.01-6.93 (1H, m), 6.33 (1H, d, J=2.8 Hz), 5.88 (2H, s);
¹³C NMR (DMSO-d₆) δ ppm 173.14, 152.86, 136.71, 136.42, 128.02, 126.45, 125.83, 121.61, 119.67, 119.16, 114.36, 111.95, 109.51, 97.74, 46.31;
MS (ESI) m/z 295 (M−1).

Example 22

1-(1H-Benzimidazol-2-ylmethyl)-2-thioxo-1,2,3,5-tetrahydro-pyrrolo[3,2-d]pyrimidin-4-one (a) Ethyl 3-[(1H-benzimidazol-2-ylmethyl)amino]-1H-pyrrole-2-carboxylate A reaction mixture of 3-amino-1H-pyrrole-2-carboxylic acid ethyl ester (0.77 g, 4.99 mmol), 1H-benzoimidazole-2-carboxaldehyde (0.88 g, 5.99 mmol), NaCNBH₃ (0.31 g, 4.99 mmol) and HOAc (0.57 mL, 9.99 mmol) in methanol (15 mL) was stirred at r.t. overnight. The mixture was then heated at 50° C. for 5 h. Cooled to r.t. and evaporated in vacuo. The residue was dissolved in ethyl acetate and washed with water. The aqueous phase was extracted with ethyl acetate (twice). The combined organic layers were dried (MgSO₄) and concentrated. The crude product was purified by flash column chromatography (heptane/ethyl acetate (1:0 to 0:1), obtaining 1.15 g (81%) of the title compound.
¹H NMR (DMSO-d₆) δ ppm 12.27 (1H, s), 10.85 (1H, s), 7.63-7.37 (2H, m), 7.17-7.08 (2H, m), 6.71 (1H, t, J=3.0 Hz), 5.99 (1H, br s), 5.60 (1H, t, J=2.7 Hz), 4.48 (2H, d, J=5.8 Hz), 4.22 (2H, q, J=7.1 Hz), 1.29 (3H, t, J=7.1 Hz);
MS (ESI) m/z 285 (M+1).

(b) 1-(1H-Benzimidazol-2-ylmethyl)-2-thioxo-1,2,3,5-tetrahydro-pyrrolo[3,2-d]pyrimidin-4-one Ethyl 3-[(1H-benzimidazol-2-ylmethyl)amino]-1H-pyrrole-2-carboxylate (0.33 g, 1.16 mmol) was added to CH₂Cl₂ (3 mL) and methanol was added until clear solution was obtained. The solution was stirred at r.t. for 1 h. Benzoyl isothiocyanate (0.73 mL, 0.46 mmol) was added and after stirring at r.t. for 30 minutes the mixture was concentrated. The residue was dissolved in ammonia (7N in methanol, 7 mL) and the mixture was heated at 80° C. in a sealed steel container for 2 h. After cooling to r.t. the precipitated product was filtrated and washed through with methanol, diethyl ether and ethyl acetate, obtaining 0.23 g (66%) of the title compound as a white solid.
¹H NMR (DMSO-d₆) δ ppm 12.27 (3H, br s), 7.61-7.37 (2H, m), 7.43-7.27 (1H, m), 7.18-7.07 (2H, m), 6.19 (1H, d, J=2.8 Hz), 5.89 (2H, s);
MS (ESI) m/z 298 (M+1).

Example 23

1-[(5-Chloro-1H-indol-2-yl)methyl]-2-thioxo-1,2,3,5-tetrahydro-pyrrolo[3,2-d]pyrimidin-4-one 5-Chloro-1H-indole-2-carbaldehyde (0.15 g, 0.76 mmol), NaCNBH₃ (0.040 g, 0.63 mmol) and Et₃N (0.088 mL, 0.63 mmol) was added to a stirred solution of 3-amino-1H-pyrrole-2-carboxylic acid ethyl ester hydrochloride (0.12 g, 0.63 mmol) in methanol (3 mL). The resulting mixture was stirred at r.t. overnight. The reaction mixture was heated to 50° C. Additional NaCNBH₃ (0.5 equiv.) was added and the mixture was stirred at 50° C. for 3 h. A few drops of HOAc was added, and after 1 h the reaction mixture was cooled to r.t. and was concentrated in vacuo. The residue was dissolved in CH₂Cl₂ (2 mL) and methanol (2 mL). Benzoyl isothiocyanate (0.093 mL, 0.69 mmol) was added and after stirring at r.t. for 1 h the mixture was concentrated in vacuo. The residue was dissolved in ammonia (7N in methanol, 3 mL) and heated at 80° C. for 2 h. The precipitated product was filtered and washed through with methanol and diethyl ether, followed by purification by preparative HPLC, obtaining 0.063 g (30%) of the title compound as a solid.

$^1$H NMR (DMSO-d$_6$) δ ppm 12.41 (2H, br s), 11.51-11.04 (1H, m), 7.51-7.46 (1H, m), 7.40-7.33 (1H, m), 7.33-7.30 (1H, m), 7.07-6.99 (1H, m), 6.34-6.27 (2H, m), 5.87-5.80 (2H, m);

$^{13}$C NMR (DMSO-d$_6$) δ ppm 173.65, 153.05, 136.84, 135.98, 134.74, 129.28, 128.27, 123.97, 121.26, 119.19, 114.24, 113.25, 100.33, 97.17, 47.31;

MS (ESI) m/z 331 (M+1).

Example 24

1-[(5-Fluoro-1H-indol-2-yl)methyl]-2-thioxo-1,2,3,5-tetrahydro-pyrrolo[3,2-d]pyrimidin-4-one The title compound was obtained as a solid in 19% (0.038 g) yield and was prepared in accordance with the general method of Example 23 using 3-amino-1H-pyrrole-2-carboxylic acid ethyl ester hydrochloride (0.12 g, 0.63 mmol), 5-fluoro-1H-indole-2-carbaldehyde (0.12 g, 0.76 mmol), NaCNBH$_3$ (0.040 g, 0.63 mmol, +0.5 equiv.), Et$_3$N (0.088 mL, 0.63 mmol) and benzoyl isothiocyanate (0.093 mL, 0.69 mmol).

$^1$H NMR (DMSO-d$_6$) δ ppm 12.38 (2H, br s), 11.10 (1H, s), 7.41-7.26 (2H, m), 7.25-7.11 (1H, m), 6.96-6.79 (1H, m), 6.37-6.24 (2H, m), 5.83 (2H, s);

$^{13}$C NMR (DMSO-d$_6$) δ ppm 173.61, 173.81, 158.46, 156.17, 152.94, 136.85, 136.10, 132.94, 128.39, 128.30, 114.19, 112.71, 112.61, 109.54, 109.28, 104.75, 104.51, 100.82, 100.78, 97.23, 47.35;

MS (ESI) m/z 315 (M+1).

Example 25

1-(1H-Indol-6-ylmethyl)-2-thioxo-1,2,3,5-tetrahydro-pyrrolo[3,2-d]pyrimidin-4-one The title compound obtained as a solid in 19% (0.035 g) yield and was prepared in accordance with the general method of Example 23 using 3-amino-1H-pyrrole-2-carboxylic acid ethyl ester hydrochloride (0.12 g, 0.63 mmol), 6-formylindole (0.11 g, 0.76 mmol), NaCNBH$_3$ (0.040 g, 0.63 mmol, +0.5 equiv.), Et$_3$N (0.088 mL, 0.63 mmol) and benzoyl isothiocyanate (0.093 mL, 0.69 mmol).

$^1$H NMR (DMSO-d$_6$) δ ppm 12.37 (2H, br s), 11.01 (1H, s), 7.53-7.43 (1H, m), 7.33 (1H, s), 7.32-7.25 (2H, m), 7.09-7.03 (1H, m), 6.41-6.34 (1H, m), 6.17 (1H, d, J=2.8 Hz), 5.79 (2H, s);

$^{13}$C NMR (DMSO-d$_6$) δ ppm 173.76, 152.91, 137.06, 136.21, 128.88, 128.27, 127.31, 125.99, 120.35, 118.91, 114.16, 110.24, 101.28, 97.63, 53.32;

MS (ESI) m/z 297 (M+1).

Example 26

1-(1H-Indol-5-ylmethyl)-2-thioxo-1,2,3,5-tetrahydro-pyrrolo[3,2-d]pyrimidin-4-one The title compound was obtained as a solid in 39% (0.073 g) yield and was prepared in accordance with the general method of Example 23 using 3-amino-1H-pyrrole-2-carboxylic acid ethyl ester hydrochloride (0.12 g, 0.63 mmol), 5-formylindole (0.11 g, 0.76 mmol), NaCNBH$_3$ (0.040 g, 0.63 mmol, +0.5 equiv.), Et$_3$N (0.088 mL, 0.63 mmol) and benzoyl isothiocyanate (0.093 mL, 0.69 mmol).

$^1$H NMR (DMSO-d$_6$) δ ppm 12.33 (2H, br s), 11.07 (1H, s), 7.52 (1H, s), 7.36-7.29 (2H, m), 7.29-7.25 (1H, m), 7.21-7.12 (1H, m), 6.39-6.34 (1H, m), 6.21-6.16 (1H, m), 5.77 (2H, s);

$^{13}$C NMR (DMSO-d$_6$) δ ppm 173.32, 152.51, 136.63, 135.20, 127.83, 127.50, 126.15, 125.81, 120.54, 118.81, 113.82, 111.40, 101.00, 97.28, 52.99;

MS (ESI) m/z 297 (M+1).

Example 27

1-[(5-Fluoro-1H-indol-3-yl)methyl]-2-thioxo-1,2,3,5-tetrahydro-pyrrolo[3,2-d]pyrimidin-4-one 3-Amino-1H-pyrrole-2-carboxylic acid ethyl ester hydrochloride (0.10 g, 0.52 mmol) was dissolved in methanol (4 mL) and 5-fluoro-1H-indole-3-carboxaldehyde (0.10 g, 0.63 mmol), NaCNBH$_3$ (0.033 g, 0.52 mmol) and Et$_3$N (0.073 g, 0.52 mmol) were added. The resulting mixture was stirred at r.t. overnight. Additional NaCNBH$_3$ (0.01 g) was added and the mixture was heated at 50° C. for 5 h. The reaction mixture was cooled to r.t. and concentrated in vacuo. The crude intermediate was dissolved in CH$_2$Cl$_2$ (3 mL) and methanol (1 mL). Benzoyl isothiocyanate (0.078 mL, 0.58 mmol) was added and after stirring at r.t. for 1 h the mixture was concentrated in vacuo. The residue was dissolved in ammonia (7N in methanol, 3 mL) and heated at 80° C. for 2 h. The solvent was removed in vacuo and after purification by preparative, HPLC, the title compound (0.035 g, 21%) was obtained as a solid.

$^1$H NMR (DMSO-d$_6$) δ ppm 12.29 (2H, s), 11.38-11.08 (1H, m), 7.76-7.68 (1H, m), 7.65-7.59 (1H, m), 7.37-7.30 (1H, m), 7.30-7.27 (1H, m), 6.96-6.86 (1H, m), 6.37 (1H, d, J=2.8 Hz), 5.84 (2H, s);

$^{13}$C NMR (DMSO-d$_6$) δ ppm 173.09, 158.27, 155.97, 152.81, 136.59, 133.11, 128.14, 128.09, 126.70, 126.59, 114.37, 113.01, 112.91, 109.95, 109.91, 109.86, 109.68, 104.70, 104.46, 97.74, 46.10;

MS (ESI) m/z 315 (M+1).

Example 28

1-(1H-Imidazol-5-ylmethyl)-2-thioxo-1,2,3,5-tetrahydro-pyrrolo[3,2-d]pyrimidin-4-one 3-Amino-1H-pyrrole-2-carboxylic acid ethyl ester hydrochloride (0.10 g, 0.52 mmol) was dissolved in methanol (4 mL) and 4-formylimidazole (0.060 g, 0.63 mmol), NaCNBH$_3$ (0.033 g, 0.52 mmol) and Et$_3$N (0.073 g, 0.52 mmol) were added. The resulting mixture was stirred at r.t. overnight. The solvent was removed in vacuo and the residue was dissolved in CH$_2$Cl$_2$ (3 mL) and methanol (1 mL). Benzoyl isothiocyanate (0.078 mL, 0.58 mmol) was added and after stirring at r.t. for 30 minutes the mixture was concentrated in vacuo. The residue was dissolved in ammonia (7N in methanol, 3 mL) and heated at 80° C. for 1 h. The precipitated product was filtered and washed with methanol, followed by diethyl ether. The crude product was purified by preparative HPLC, obtaining 0.017 g (13%) of the title compound as a solid.

OC 710/07

$^1$H NMR (DMSO-d$_6$) δ ppm 12.49-11.78 (3H, m), 7.53 (1H, s), 7.30 (1H, d, J=2.8 Hz), 7.05 (1H, s), 6.36 (1H, d, J=3.0 Hz), 5.54 (2H, s);

MS (ESI) m/z 335 (M+1).

Example 29

1-(1H-Imidazol-2-ylmethyl)-2-thioxo-1,2,3,5-tetrahydro-pyrrolo[3,2-d]pyrimidin-4-one (a) Ethyl 3-[(1H-imidazol-2-ylmethyl)amino]-1H-pyrrole-2-carboxylate A reaction mixture with 3-amino-1H-pyrrole-2-carboxylic acid ethyl ester (0.2 g, 1.30 mmol), 2-imidazolecarboxaldehyde (0.15 g, 1.53 mmol), NaCNBH$_3$ (0.082 g, 1.30 mmol) and OHAc (0.15 mL, 2.60 mmol) in methanol (5 mL) was stirred at r.t. for 2 h. The solvent was evaporated in vacuo and the residue was dissolved in ethyl acetate. Washed with water and the aqueous layer was extracted twice with ethyl acetate. The combined organic layers were dried (MgSO$_4$), filtered and concentrated. The crude product was purified by flash column chromatography (CH$_2$Cl$_2$/methanol gradient; 0 to 20% methanol), obtaining 0.30 g (99%) of the title compound.

$^1$H NMR (DMSO-d$_6$) δ ppm 10.84 (1H, br s), 7.03 (2H, s), 6.79-6.64 (1H, m), 5.76 (1H, br s), 5.68-5.57 (1H, m), 4.29 (2H, d, J=5.8 Hz), 4.19 (2H, q, J=7.1 Hz), 3.16 (1H, s), 1.26 (3H, t, J=7.1 Hz);
MS (ESI) m/z 235 (M+1).

(b) 1-(1H-Imidazol-2-ylmethyl)-2-thioxo-1,2,3,5-tetrahydro-pyrrolo[3,2-d]pyrimidin-4-one Benzoyl isothiocyanate (0.19 mL, 1.41 mmol) was added to a stirred solution of ethyl 3-[(1H-imidazol-2-ylmethyl)amino]-1H-pyrrole-2-carboxylate (0.3 g, 1.28 mmol) in CH$_2$Cl$_2$ (4 mL) and methanol (2 mL) and the mixture was stirred at r.t. for 1 h. The solvent was evaporated in vacuo and the residue was dissolved in ammonia (7N in methanol, 7 mL) and heated at 80° C. for 1 h. The crude product was filtrated and purified by preparative HPLC, obtaining 0.110 g, (35%) of the title compound as a white solid.

$^1$H NMR (DMSO-d$_6$) δ ppm 12.46-12.14 (2H, m), 11.81 (1H, br s), 7.28 (1H, d, J=2.5 Hz), 6.99 (1H, s), 6.79 (1H, s), 6.13 (1H, d, J=2.8 Hz), 5.67 (2H, s);
MS (ESI) m/z 248 (M+1).

Example 30

1-[(5-Chloro-1H-benzimidazol-2-yl)methyl]-2-thioxo-1,2,3,5-tetrahydro-pyrrolo[3,2-d]pyrimidin-4-one (a) Ethyl 3-{[(5-chloro-1H-benzimidazol-2-yl)methyl]amino}-1H-pyrrole-2-carboxylate A reaction mixture of 3-amino-1H-pyrrole-2-carboxylic acid ethyl ester (0.077 g, 0.5 mmol), NaCNBH$_3$ (0.057 g, 0.9 mmol) and HOAc (0.030 g, 0.5 mmol) in methanol (4 mL) were stirred at r.t. for 5 minutes before 5-chloro-1H-benzimidazole-2-carbaldehyde (0.144 g, 0.8 mmol) was added, followed by addition of CH$_2$Cl$_2$ (1 mL) and DMF (0.4 mL). The resulting mixture was allowed to stir for 16 h at r.t. under nitrogen atmosphere. Additional 5-chloro-1H-benzimidazole-2-carbaldehyde (0.030 g) and NaCNBH$_3$ (0.015 g) were added and the reaction mixture was stirred at 4 h. The reaction mixture was neutralized with 2M NaOH and diluted with ethyl acetate. Extracted with water and the organic layer was dried (Na$_2$SO$_4$) and concentrated. The crude product was purified by flash column chromatography (heptane/ethyl acetate gradient; 0 to 100% ethyl acetate), obtaining 0.074 g (46%) of the title product.

$^1$H NMR (CDCl$_3$) δ ppm 8.28 (1H, br s), 7.52 (1H, s), 7.44 (1H, d, J=2.0 Hz), 7.22 (1H, d, J=2.0 Hz), 6.66 (1H, s), 5.61 (1H, t, J=2.4 Hz), 4.67 (2H, s), 4.27 (2H, m), 1.33 (3H, t, J=6.8 Hz);
MS (ESI) m/z 319 (M+1).

(b) 1-[(5-Chloro-1H-benzimidazol-2-yl)methyl]-2-thioxo-1,2,3,5-tetrahydro-pyrrolo[3,2-d]pyrimidin-4-one A solution of ethyl 3-{[(5-chloro-1H-benzimidazol-2-yl)methyl]amino}-1H-pyrrole-2-carboxylate (0.074 g, 0.23 mmol) in CH$_2$Cl$_2$ was stirred for 5 minutes. DMF (0.2 mL) was added to enhance solubility. Benzoyl isothiocyanate (0.045 g, 0.28 mmol) was added and the mixture was stirred for 1 h then concentrated in vacuo. The crude intermediate was taken up in ammonia (7N in methanol, 2 mL) and was stirred at 70° C. for 1.5 h in a sealed vessel. After cooling to r.t. the precipitated product was collected by vacuum filtration, washed with diethyl ether and dried, obtaining 0.033 g (43%) of the title product as a white solid.

$^1$H NMR (DMSO-d$_6$) δ ppm 12.33 (3H, br s), 1.48 (2H, m), 7.32 (1H, s), 7.17 (1H, d, J=8.0 Hz), 6.21 (1H, s), 5.88 (2H, s);
MS (ESI) m/z 332 (M+1).

Example 31

1-[(4,5-Dimethyl-1H-benzimidazol-2-yl)methyl]-2-thioxo-1,2,3,5-tetrahydro-pyrrolo[3,2-d]pyrimidin-4-one (a) 4,5-Dimethyl-1H-benzimidazole-2-carbaldehyde 3,4-Dimethylbenzene-1,2-diamine (0.409 g, 3.0 mmol) and dichloroacetic acid (0.768 g, 6.0 mmol) in 4N HCl (10 mL) were heated at 100° C. for two days. After cooling to r.t. the mixture was filtered and the mother liquor was extracted with chloroform (4 times). The pH was set to 12 using 2M NaOH and the resulting white precipitate was collected by filtration. The crude product was used in the next step without further purification.

MS (ESI) m/z 175 (M+1).

(b) Ethyl 3-{[(4,5-dimethyl-1H-benzimidazol-2-yl)methyl]amino}-1H-pyrrole-2-carboxylate 3-Amino-1H-pyrrole-2-carboxylic acid ethyl ester (0.077 g, 0.5 mmol), 4,5-dimethyl-1H-benzimidazole-2-carbaldehyde (0.130 g, 0.75 mmol) and HOAc (0.045 g, 0.75 mmol) were stirred in methanol (4 mL) followed by addition of NaCNBH$_3$. The resulting mixture was stirred at r.t. for 16 h. The reaction mixture was neutralized with 2M NaOH and the solvent was removed in vacuo. The residue was dissolved in ethyl acetate and extracted with water. The organic layer was dried (Na$_2$SO$_4$) and concentrated. The crude product was purified by flash column chromatography (heptane/ethyl acetate gradient; 0 to 100% ethyl acetate), obtaining a white solid, 0.043 g (27%) of the title compound, as a tautomeric mixture (1:1).

$^1$H NMR (DMSO-d$_6$) δ ppm 12.15 (1H, s), 12.04 (1H, s), 10.81 (2H, s), 7.26 (1H, d, J=8.4 Hz), 7.12 (1H, d=8.0 Hz), 6.94 (2H, d, J=8.4 Hz), 6.72 (2H, s), 5.93 (2H, s), 5.70 (1H, s), 5.61 (1H, s), 4.44 (4H, dd, J=9.2, 6.0 Hz), 4.22 (4H, m), 2.44 (3H, s), 2.37 (3H, s), 2.29 (6H, s), 1.30 (6H, m);
MS (ESI) m/z 313 (M+1).

(c) 1-[(4,5-Dimethyl-1H-benzimidazol-2-yl)methyl]-2-thioxo-1,2,3,5-tetrahydro-pyrrolo[3,2-d]pyrimidin-4-one Ethyl 3-{[(4,5-dimethyl-1H-benzimidazol-2-yl)methyl]amino}-1H-pyrrole-2-carboxylate (0.043 g, 0.14 mmol) was dissolved in $CH_2Cl_2$ (1.5 mL) and benzoyl isothiocyanate (0.026 g, 0.16 mmol) was added. After stirring at r.t. for 1 h the solvent was removed in vacuo. The residue was dissolved in ammonia (7N in methanol) and heated to 70° C. for 2 h in a sealed vessel. The solvent was removed in vacuo and the residue was purified by preparative HPLC, obtaining a white solid, 0.008 g (18%) of the title compound, as a tautomeric mixture (1:1).

$^1$H NMR (DMSO-$d_6$) δ ppm 12.18 (2H, s), 11.98 (2H, s), 7.28 (2H, t, J=2.4 Hz), 7.19 (1H, d, J=8.0 Hz), 7.08 (1H, d, J=8.0 Hz), 6.92 (2H, t, J=8.0 Hz), 6.14 (2H, dd, J=8.0, 2.8 Hz), 5.89 (2H, s), 5.86 (2H, s), 2.41 (3H, s), 2.37 (3H, s), 2.29 (3H, s), 2.28 (3H, s);

MS (ESI) m/z 326 (M+1).

Example 32

7-Bromo-1-isobutyl-2-thioxo-1,2,3,5-tetrahydro-pyrrolo[3,2-d]pyrimidin-4-one

(a) 3-Amino-4-bromo-1H-pyrrole-2-carboxylic acid ethyl ester

3-Amino-1H-pyrrole-2-carboxylic acid ethyl ester (0.92 g, 0.6 mmol) was dissolved in HOAc (1 mL) and bromine water (0.96 g, 0.6 mmol) was added. The mixture was stirred for 1 h at r.t., and the resulted white precipitate was collected by filtration and washed with diethyl ether. The title compound (0.136 g, 97%) was obtained as a white solid and used in the next step without further purification.

$^1$H NMR (DMSO-$d_6$) δ ppm 11.67 (1H, s), 7.05 (1H, s), 6.02 (2H, br s), 4.25 (2H, q, J=7.2 Hz), 1.28 (3H, t, J=7.2 Hz);

MS (ESI) m/z 233 (M+1).

(b) 4-Bromo-3-(isobutylamino)-1H-pyrrole-2-carboxylic acid ethyl ester

3-Amino-4-bromo-1H-pyrrole-2-carboxylic acid ethyl ester (0.136 g, 0.58 mmol) and isobutyraldehyde (0.067 g, 0.93 mmol) were stirred in $CH_2Cl_2$/MeOH (1:1, 3 mL) at r.t. for 2 h. NaCNBH$_3$ (0.065 g, 1.04 mmol) and HOAc (0.035 g, 0.58 mmol) were added and the mixture was stirred at r.t. for 2 h and then stirred at 50° C. for 16 h. Additional isobutyraldehyde (1 equiv.) and NaCNBH$_3$ (0.5 equiv.) were added and the mixture was continued stirring at 50° C. overnight. The reaction mixture was neutralized with 2 M NaOH solution and the solvents were removed in vacuo. The residue was taken up in ethyl acetate and extracted with water. The organic layer was dried (Na$_2$SO$_4$) and concentrated. The crude product was purified by flash chromatography (heptane/ethyl acetate gradient, 0 to 30% ethyl acetate), obtaining the title compound (0.040 g, 24%) as a white solid.

$^1$H NMR (CDCl$_3$) δ ppm 6.75 (1H, s), 4.32 (2H, q, J=7.2 Hz), 3.28 (2H, d, J=6.8 Hz), 1.85 (1H, m), 1.35 (3H, t, J=7.2 Hz), 0.97 (3H, d, J=6.8 Hz);

MS (ESI) m/z 289 (M+1).

(c) 7-Bromo-1-isobutyl-2-thioxo-1,2,3,5-tetrahydro-pyrrolo[3,2-d]pyrimidin-4-one Benzoyl isothiocyanate (0.034 g, 0.2 mmol) was added to a solution of 4-bromo-3-(isobutylamino)-1H-pyrrole-2-carboxylic acid ethyl ester (0.050 g, 0.17 mmol) in $CH_2Cl_2$ and the resulting mixture was stirred at r.t. for 1 h before it was concentrated in vacuo. The residue was dissolved in ammonia (7M in methanol, 1.5 mL) and stirred at 70° C. for 4 h. Additional ammonia (7M in methanol, 1 mL) was added and the mixture was stirred at 80° C. for 5 h. The mixture was cooled to r.t. and the precipitated product was filtered and washed with diethyl ether. After recrystallization with methanol the title compound (0.028 g, 55%) was obtained as a white solid.

$^1$H NMR (DMSO-$d_6$) δ ppm 12 57 (2H, br s), 7.58 (1H, s), 4.92 (1H, br s), 4.42 (1H, br s), 2.39 (1H, m), 0.94 (6H, d, J=6.4 Hz);

MS (ESI) m/z 303 (M+1).

Example 33

1-(3-Chlorophenyl)-2-thioxo-1,2,3,5-tetrahydro-pyrrolo[3,2-d]pyrimidin-4-one

(a) Ethyl 3-[(3-chlorophenyl)amino]-1H-pyrrole-2-carboxylate

A mixture of 3-amino-1H-pyrrole-2-carboxylic acid ethyl ester (0.20 g, 1.3 mmol), 3-bromochlorobenzene (0.30 g, 1.6 mmol), Pd$_2$(dba)$_3$ (0.048 g, 0.052 mmol), rac-BINAP (0.048 g, 0.078 mmol) and cesium carbonate (0.59 g, 1.8 mmol) was heated at 100° C. in a sealed microwave vial under nitrogen atmosphere overnight. Additional Pd$_2$(dba)$_3$ (0.10 g, 0.11 mmol) and R,S-BINAP (0.11 g, 0.18 mmol) were added and the reaction was continued stirring at 100° C. overnight. Additional 3-bromochlorobenzene (0.15 g), Pd$_2$(dba)$_3$ (0.098 g) and R,S-BINAP (0.098 g) were added and the reaction was continued stirring at 100° C. for three more days. The reaction mixture was poured into ethanol and the resulting solution was filtered. The filtrate was evaporated in vacuo and the residue was purified by flash column chromatography (heptane/ethyl acetate gradient; 0 to 30% ethyl acetate), obtaining 0.052 g (15%) of the title compound.

$^1$H NMR (CDCl$_3$) δ ppm 8.42 (1H, br s), 7.17 (1H, t, J=8.0 Hz), 7.14 (1H, t, J=2.0 Hz), 6.96-6.94 (1H, m), 6.87-6.84 (1H, m), 6.82 (1H, t, J=3.0 Hz), 6.32 (1H, t, J=3.0 Hz), 4.35 (2H, q, J=7.2 Hz), 1.38 (3H, t, J=7.1 Hz);

MS (ESI) m/z 263 (M−1).

(b) 1-(3-Chlorophenyl)-2-thioxo-1,2,3,5-tetrahydro-pyrrolo[3,2-d]pyrimidin-4-one Benzoyl isothiocyanate (0.035 g, 0.22 mmol) in $CH_2Cl_2$ (0.5 mL) was added to ethyl 3-[(3-chlorophenyl)amino]-1H-pyrrole-2-carboxylate (0.052 g, 0.20 mmol) in $CH_2Cl_2$ (0.5 mL). The mixture was stirred at r.t. overnight. Additional benzoyl isothiocyanate (0.035 g+0.035 g+0.035 g) were added over 6 h and the reaction was continued stirring at 50° C. for 3 days. The solvent was removed in vacuo and the residue was dissolved in ammonia (7N in methanol, 4 mL). The reaction was heated at 50° C. for 2 h. The crude product was purified by preparative chromatography, obtaining 0.009 g (15%) of the title compound as a solid.

$^1$H NMR (DMSO-$d_6$) δ ppm 12.41 (2H, br s), 7.60-7.57 (3H, m), 7.41-7.37 (1H, m), 7.25 (1H, d, J=2.8 Hz), 5.36 (1H, d, J=2.8 Hz);

$^{13}$C NMR (DMSO-d$_6$) δ ppm 173.8, 152.8, 141.5, 137.9, 133.5, 131.3, 129.0, 128.6, 127.7, 127.3, 113.3, 96.7;

MS (ESI) m/z 278 (M+1).

Screens

Methods for the determination of MPO inhibitory activity are disclosed in patent application WO 02/090575. The pharmacological activity of compounds according to the invention was tested in the following screen in which the compounds were either tested alone or in the presence of added tyrosine:

Assay buffer: 20 mM sodium/potassium phosphate buffer pH 6.5 containing 10 mM taurine and 100 mM NaCl.

Developing reagent: 2 mM 3,3',5,5'-tetramethylbenzidine (TMB), 200 µM KI, 200 mM acetate buffer pH 5.4 with 20% DMF.

To 10 µl of diluted compounds in assay buffer, 40 µl of human MPO (final concentration 2.5 nM), with or without 20 µM tyrosine (final concentration, if present, 8 µM), was added and the mixture was incubated for 10 minutes at ambient temperature. Then 50 µl of H$_2$O$_2$ (final concentration 100 µM), or assay buffer alone as a control, were added. After incubation for 10 minutes at ambient temperature, the reaction was stopped by adding 10 µl 0.2 mg/ml of catalase (final concentration 18 µg/ml). The reaction mixture was left for an additional 5 minutes before 100 µl of TMB developing reagent was added. The amount of oxidised 3,3',5,5'-tetramethylbenzidine formed was then measured after about 5 minutes using absorbance spectroscopy at about 650 nM. IC$_{50}$ values were then determined using standard procedures.

When tested in at least one version of the above screen, the compounds of Examples 1 to 32 gave IC$_{50}$ values of less than 60 µM, indicating that they are expected to show useful therapeutic activity. Representative results are shown in the following Table.

| Compound | Inhibition of MPO (in the presence of tyrosine) IC50 µM |
| --- | --- |
| Example 2 | 0.26 |
| Example 5 | 0.22 |
| Example 11 | 1.1 |

The invention claimed is:

1. A compound of the following formula

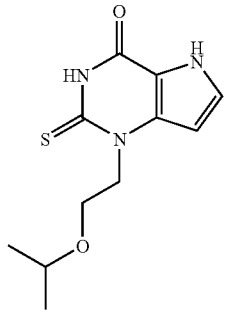

or a pharmaceutically acceptable salt thereof.

* * * * *